(12) United States Patent
Goldsmith

(10) Patent No.: US 11,092,598 B2
(45) Date of Patent: Aug. 17, 2021

(54) CHEMICALLY DIFFERENTIATED SENSOR ARRAY

(71) Applicant: Cardea Bio, Inc., San Diego, CA (US)

(72) Inventor: Brett Goldsmith, San Diego, CA (US)

(73) Assignee: Cardea Bio, Inc., San Diego, CA (US)

( * ) Notice: Subject to any disclaimer, the term of this patent is extended or adjusted under 35 U.S.C. 154(b) by 0 days.

(21) Appl. No.: 15/589,942

(22) Filed: May 8, 2017

(65) Prior Publication Data

US 2017/0307562 A1 Oct. 26, 2017

Related U.S. Application Data

(63) Continuation of application No. 14/884,705, filed on Oct. 15, 2015, now abandoned, which is a
(Continued)

(51) Int. Cl.
| | | |
|---|---|---|
| *G01N 33/543* | (2006.01) | |
| *G01N 27/414* | (2006.01) | |
| *C12Q 1/6869* | (2018.01) | |
| *G01N 33/02* | (2006.01) | |
| *G01N 33/483* | (2006.01) | |

(Continued)

(52) U.S. Cl.
CPC ..... *G01N 33/54373* (2013.01); *C12Q 1/6869* (2013.01); *G01N 27/4145* (2013.01); *G01N 27/4148* (2013.01); *G01N 33/02* (2013.01); *G01N 33/4836* (2013.01);
(Continued)

(58) Field of Classification Search
None
See application file for complete search history.

(56) References Cited

U.S. PATENT DOCUMENTS

| | | | |
|---|---|---|---|
| 6,150,106 A * | 11/2000 | Martin | G01N 33/5438 204/450 |
| 8,445,945 B2 | 5/2013 | Rothberg et al. | |

(Continued)

FOREIGN PATENT DOCUMENTS

| | | |
|---|---|---|
| CN | 103323494 A | 9/2013 |
| CN | 104101626 A | 10/2014 |

(Continued)

OTHER PUBLICATIONS

Patent Cooperation Treaty, International Search Report for PCT/US2016/026730, dated Jul. 15, 2016, pp. 1-2.
(Continued)

*Primary Examiner* — Melanie Brown
(74) *Attorney, Agent, or Firm* — Kunzler Bean & Adamson

(57) ABSTRACT

A chemically differentiated sensor array system includes a plurality of environmentally-gated transistors and an environmental gate, wherein the environmental gate includes a liquid solution and each environmentally-gated transistor includes a drain, a source, and a Carbon-based substrate channel, the drain electrically couples to a first location on the substrate channel, the source electrically couples to a second location on the substrate channel separated by a gap from the first location on the substrate channel, the environmental gate covers and contacts the substrate channel, a first insulating layer covers and separates the drain from the environmental gate, and a second insulating layer covers and separates the source from the environmental gate.

18 Claims, 24 Drawing Sheets

Related U.S. Application Data continuation-in-part of application No. 14/263,954, filed on Apr. 28, 2014, now Pat. No. 9,618,476, and a continuation-in-part of application No. 14/684,283, filed on Apr. 10, 2015, now Pat. No. 9,765,395.

(51) Int. Cl.
  *G01N 33/49* (2006.01)
  *G01N 33/493* (2006.01)

(52) U.S. Cl.
  CPC .......... *G01N 33/49* (2013.01); *G01N 33/493* (2013.01); *G01N 33/5438* (2013.01)

(56) References Cited

U.S. PATENT DOCUMENTS

| | | | |
|---|---|---|---|
| 8,716,029 B1* | 5/2014 | Kim | G01N 33/5306 436/501 |
| 2004/0238379 A1 | 12/2004 | Lindsay et al. | |
| 2010/0133510 A1 | 6/2010 | Kim et al. | |
| 2010/0248209 A1 | 9/2010 | Datta et al. | |
| 2010/0255984 A1 | 10/2010 | Sutter et al. | |
| 2010/0279426 A1 | 11/2010 | Tour | |
| 2010/0327847 A1 | 12/2010 | Leiber et al. | |
| 2011/0165557 A1 | 7/2011 | Ah et al. | |
| 2011/0217763 A1 | 9/2011 | Rasooly et al. | |
| 2012/0143027 A1 | 6/2012 | Phillips et al. | |
| 2012/0214172 A1 | 8/2012 | Chen et al. | |
| 2012/0220053 A1 | 8/2012 | Lee et al. | |
| 2013/0089932 A1 | 4/2013 | Wu et al. | |
| 2013/0204107 A1 | 8/2013 | Lee et al. | |
| 2013/0270521 A1 | 10/2013 | Peng et al. | |
| 2014/0042390 A1 | 2/2014 | Gruner et al. | |
| 2014/0162390 A1 | 6/2014 | Afzali-Ardakani et al. | |
| 2014/0312879 A1 | 10/2014 | Torsi et al. | |
| 2015/0038378 A1 | 2/2015 | Cheng et al. | |
| 2015/0218094 A1 | 8/2015 | Braunschweig et al. | |
| 2015/0247819 A1* | 9/2015 | Shi | G01N 27/4145 506/12 |
| 2015/0276709 A1 | 10/2015 | O'Halloran et al. | |
| 2015/0316523 A1 | 11/2015 | Patolsky et al. | |
| 2016/0123919 A1 | 5/2016 | Johnson et al. | |
| 2016/0290955 A1 | 10/2016 | Zhong et al. | |

FOREIGN PATENT DOCUMENTS

| | | |
|---|---|---|
| KR | 20100107087 | 10/2010 |
| WO | 2012050646 A2 | 4/2012 |
| WO | 2012112746 A1 | 8/2012 |

OTHER PUBLICATIONS

Nguyen et al. "Graphene Interfaced with Biological Cells: Opportunities and Challenges," The 5 Journal of Physical Chemistry Letters, 2012, vol. 3, pp. 1024-1029.

Mohanty et al. "Graphene-Based Single-Bacterium Resolution Biodevice and DNA Transistor: Interfacing Graphene Derivatives with Nanoscale and Microscale Biocomponents" Nano Lett., Nov. 5, 2008, vol. 8, No. 12, pp. 4469-4476.

Patent Cooperation Treaty, International Search Report for PCT/US2015/026254, dated Jul. 16, 2015, pp. 1-2.

European Patent Office, Supplementary Partial European Search Report, dated Oct. 25, 2017, pp. 1-15.

B.R. Goldsmith, "Digital Biosensing by Foundry-Fabricated Graphene Sensors", Nature.com/scientificreports, Jan. 22, 2019, pp. 1-10.

\* cited by examiner

CHEMICALLY DIFFERENTIATED SENSOR ARRAY

CROSS-REFERENCE TO RELATED APPLICATIONS

This application is a continuation of U.S. patent application Ser. No. 14/884,705, filed Oct. 15, 2015, which is a continuation-in-part of U.S. patent application Ser. Nos. 14/263,954, filed Apr. 28, 2014 and 14/684,283, filed Apr. 10, 2015, the contents of which are hereby incorporated by reference in their entireties.

TECHNICAL FIELD

The present disclosure is directed towards electronic sensors for sample analysis, and more particularly, to a chemically differentiated sensor array.

BACKGROUND

Individual electronic chemical sensors may be designed to be specific for a single target chemical, broadly responsive to a class of chemicals, or have enhanced sensitivity for particular chemical interactions. Generally, there is a trade-off in making these design decisions. It may be difficult or impossible to create a single sensor with the desired chemical specificity and sensitivity. To overcome this challenge, it is common to use multiple sensors together in an array.

Creating a chemically differentiated sensor array is more complex than creation of a single sensor. This increase in complexity drives electronic sensor array design toward simpler types of sensors such as resistive or capacitive sensors. Such sensors are less sensitive than transistors or other "gated" sensors. Arrays of transistor-based chemical sensors incorporate internal gating structures such as floating gates, split gates, or back gates. This design increases manufacturing cost and complexity.

Typically, modern transistors comprise semiconducting material on a single solid or connected piece of material. There is usually a solid mechanical connection between the transistor channel, the material forming the connection for the source and drain of the transistor, the gate dielectric material, and the gate material. When incorporating transistors into sensors, this structure is usually maintained. In an ion-sensitive field effect transistor (ISFET) geometry, the gate material itself may be a liquid that is not mechanically bound to the chip. However, these types of transistors have generally included a dielectric or insulating layer mechanically bound to the transistor conduction channel to prevent unwanted chemical reactions and current flow from the gate to the transistor conduction channel. For example, silicon reacts spontaneously with oxygen when exposed to air or water, so a layer of metal oxide may be used to prevent reactions in the conduction channel. These chemically protective layers also separate the conduction channel of a transistor from the local environment when used as a sensor. This decreases the sensitivity of transistor-based chemical sensors by creating a physical barrier to interaction of the local environment to be sensed and the conduction electrons. Furthermore, these barrier layers are applied uniformly across the sensor array, limiting the available chemical differentiation between different sensors in the array.

One method of increasing chemical coupling to a sensor channel has been to reduce the insulating dielectric to a small, non-zero thickness that still chemically protects the conduction channel. This approach can be done through control of material deposition, use of specialty materials, or removal of excess gate dielectric material. This generally requires additional manufacturing steps and does not completely solve the problem.

Another method employs the use of "high-k" dielectrics such as hafnium oxide. These materials lead to a larger capacitance between the sensing environment and the conduction channel, without decreasing the thickness of the dielectric material, but again results in a chemically uniform approach that only mitigates the problem.

Another method involves creating a conductive "floating gate" that may comprise metal or some material that closely coordinates with the chemicals targeted for sensing. This approach allows for close coupling of the sensing environment to a material which is coupled to the conduction channel, but is complicated to manufacture and still requires an intermediary material to translate chemical changes to the transistor conduction channel.

SUMMARY OF EMBODIMENTS

The present disclosure is directed towards electronic sensors for sample analysis, and more particularly, to a chemically differentiated sensor array. In particular, the present disclosure is directed towards chemically differentiated sensor arrays comprising transistor-based sensors that each include an environmental gate without the need for a barrier layer or universal gate dielectric.

As disclosed herein, an environmental gate may be a liquid material that comes into contact with the transistor, has a controlled voltage, but is applied or exposed to the transistor only part of the sensing measurement. It may be a material such as water based solutions, alcohol based solutions, battery electrolyte, blood or blood derivatives, urine, bacterial growth media, food, ionic solvents, or liquid metals. The voltage of the liquid compared to the transistor channel is controlled through an external connection or through a connection elsewhere on the sensor chip. The measurement signal of these sensors is a combination of transistor transconductance, threshold voltage, and on-state resistance. Using a graphene transistor in combination with an environmental gate yields a transistor with a gate dielectric formed from the electrochemical double layer that spontaneously forms by a water when in contact with a surface. Charge transfer between the liquid and the graphene is suppressed when the graphene is clean and free of any intervening materials such as acrylic residue or dielectric material. A sensitization layer such as a polymer or protein may be applied to this clean graphene surface to impart chemical selectivity to the transistor based sensor.

Multiple transistor-based sensors may be placed in an array exposed to the same, or different environmental gates. For example, the array may include two transistors, or may include thousands of transistors. In this configuration, no barrier, protective layer or sensitization layer is required between the environmental gate and the transistor channel. However, different transistors within the array may be differentiated by employing a different sensitization layer. For example, a thick material such as an antibody layer may be used, or a thin material such as a small molecule may also be used. Each sensitization layer may be employed on a different transistor located on the same chip, and sharing the same environmental gate.

In some examples, different sensitization layers and different types of sensitization layers may be employed, including covalently and non-covalently bound materials, and incorporate them all into different groups of transistors on the same chip and sharing the same environmental gate. Signals generated by each of the transistors may read out simultaneously or nearly simultaneously (e.g., by measuring electrical properties such as voltage or current across the transistor.

In some examples, a chemically differentiated sensor array may be used as a system for biological sample analysis. For example, a system for biological sample analysis may include an electronic biological sample sensor system wherein the biological sample sensor system includes one or more sensor chips electronically coupled to an external connector wherein the sensor chips includes one or more transistors. Sequencing probes are associated with the transistors and configured such that if a complimentary DNA sequence is present in a biological sample, such as a suspension containing a DNA sample, the electrical properties of the transistor will change. Based on this change, the DNA sequence in the biological sample may be identified. The sensor system may be enclosed in a case, wherein one or more sample wells are disposed on one side, and each sample well is configured to form a liquid-tight seal with one of the sensor chips.

Also as disclosed herein, an example method for biological sample analysis. A biological sample is introduced into one or more sample wells configured to form a seal with a sensor. The sensor has a plurality of sequencing probes, configured to bind with a complementary sequence of nucleotides in a biological sample. A voltage is applied to the sensor and the output current of the sensor is measured to determine changes in the electrical properties of the sensor chip, such as the transconductance and resistance of the chip, resulting from changes in pH indicative of DNA binding. The DNA sequence of the biological sample is then identified based on the changes in the electrical properties caused by the DNA binding process.

Also as disclosed herein, an example system for biological sample analysis includes a sensing section including one or more sensor chips, wherein each sensor chip comprises one or more transistors and a plurality of sequencing probes; a plate section including one or more biological sample wells, wherein each of the one or more biological sample wells is configured to direct a liquid sample to one of the one or more sensor chips; and a processing section including a processing module.

BRIEF DESCRIPTION OF DRAWINGS

The present disclosure, in accordance with one or more various embodiments, is described in detail with reference to the following figures. The figures are provided for purposes of illustration only and merely depict typical or example embodiments of the disclosure.

Figure 1:
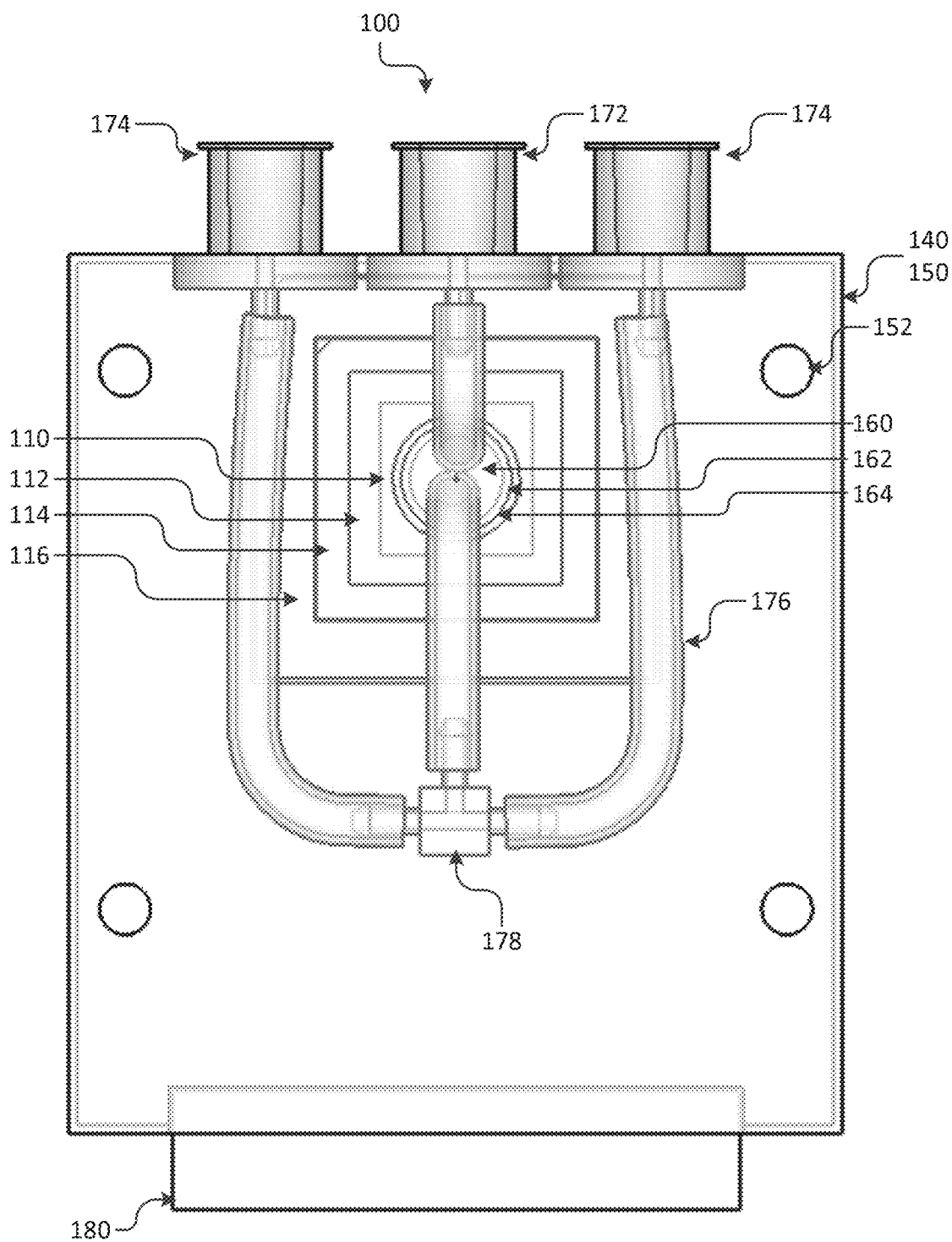
FIG. 1 illustrates a top view of a biological sample analysis device consistent with embodiments disclosed herein.

The figures are not intended to be exhaustive or to limit the disclosure to the precise form disclosed. It should be understood that the disclosure can be practiced with modification and alteration, and that the disclosure can be limited only by the claims and the equivalents thereof.

DETAILED DESCRIPTION

Embodiments of the present disclosure are directed toward a chemically differentiated sensor array. The array may include a plurality of environmentally-gated transistors and an environmental gate covering the transistors. For example, the environmental gate may be a liquid, such as a solution or a liquid metal. The solution may be water-based or alcohol-based. In some examples, the solution is a biological sample, such as blood, DNA, urine, saliva, or a cellular sample.

Each environmentally-gated transistor may include a drain, a source, and a substrate channel. The substrate channel may include a semiconductor material that is inert in air and water. For example, the semiconductor material may be Carbon-based, such as Graphene or Carbon nanotubes. The drain and source may also include semiconductor materials. For example, the drain and source may both be either n-type or p-type semiconductors. The drain and source may each be located on (e.g., deposited on) and electrically couple to the substrate channel. The drain and source are separated on the substrate channel by a gap. An insulating layer may then be deposited on, and thereby cover each of the source and the drain. When the environmental gate is filled in the gap between the source and the drain, the insulating layer separates, and thereby electrically insulates, the source and drain from the environmental gate.

The environmental gate may then electrically interact with the substrate channel. A gate electrode may then be inserted in or otherwise contact the environmental gate. Each of the source and the drain may also couple to a source lead and drain lead, respectively. A voltage may then be applied, via a power supply, to the environmental gate with respect to either the source or the drain. Based on a the type of environmental gate used, the threshold voltage required to enable current flow through the substrate channel may vary, thus enabling the environmentally-gated transistor to identify the type of environmental gate, or components of the environmental gate.

In some examples, one or more of the environmentally-gated transistors includes a sensitization layer that covers and separates the substrate channel from the environmental gate. For example, the sensitization layer may be a polymer or a protein. Different sensitization layers may be used to target different types of environmental gate substances (i.e., to increase sensitivity and specificity of a particular environmentally-gated transistor to a particular sample(s) within the environmental gate). By changing the composition or dimensions of the sensitization layer, the environmental gate's interaction with the channel substrate will change, and thus change the electrical properties of the environmentally-gated transistor. By varying the dimensions and compositions of the sensitization layers for different environmentally-gated transistor's in the array, the array can be sensitive to, and distinguish between many different substances within the environmental gate (i.e., biological molecules, antibodies, chemicals, etc.).

The system may also include an electrical measurement device electrically coupled to the source lead or drain lead of each environmentally-gated transistors. For example, the electrical measurement device may be a voltmeter, an ampmeter, or other electrical measurement device configured to measure voltage, on-site resistance, or transconductance, or other electrical properties of the transistor. One of skill in the art would understand how to configure such an electrical measurement device across an array of transistors. In some examples, the electrical measurement device is also coupled to a computing module that is configured to receive an output signal from the electrical measurement device indicating an electrical measurement value, and the identify a composition of the environmental gate based on the output signal. The computing module may include a processor and memory with a software program embedded thereon, the software being configured to perform the measurement and identification steps described above. In some examples, the computing module may also include a display and a user input device (e.g., a keyboard, mouse, etc.) to enable user interaction.

Various embodiments described below with reference to FIGS. 1-24 relate to biological sample analysis devices incorporating similar Graphene-based substrate technology to detect and identify biological samples contained within a liquid solution (similar to the environmental gate described above). FIGS. 25A and 25B below related to ion-sensitive field effect (ISFET) transistors with and without sensitization layers. FIGS. 26A, 26B, 27, and 28 relate to environmentally-gated transistors, and chemically differentiated sensor arrays that incorporate environmentally-gated transistors.

FIG. 1 illustrates a top view of an example biological sample analysis device. An example biological sample analysis device 100 an outer casing comprising a first cartridge half 140 and a second cartridge half 150 configured to fit together to form a sealed enclosure. First cartridge half 140 and second cartridge half 150 may be aligned and secured together with screws, bolts, tabs, dowels, or other fasteners inserted through mounting holes 152. For example, four mounting holes 152 in first cartridge half 140 may be aligned with four mounting holes 152 in second cartridge half 150 to properly align the two cartridge halves, and then fasteners may be inserted through the holes to secure the halves together.

The external casing of biological sample analysis device 100, in general, is configured to encapsulate an electronic biological sample sensor system enclosed therein. In some examples, the external casing of biological sample analysis device 100 may comprise an outer casing that is a single molded component wherein the molded component comprises plastic, foam, rubber, acrylic, or any other moldable material that is sufficiently watertight. In other examples, the first cartridge half 140 may be hingedly coupled to second cartridge half 150. First cartridge half 140 may also snap fit, press fit, or lock in place when oriented in a closed position with respect to second cartridge half 150 such that the two cartridge halves together form a single cartridge. In some examples, first cartridge half 140 and second cartridge half 150 are aligned using alignment pins or dowels protruding from either the first or the second of the cartridge half, and inserting said alignment pins into alignment holes 152 on the other cartridge half. In one such example, the two cartridge halves may be snap fit, form fit, or press fit together. Other methods of manufacturing a watertight external cartridge casing that are possible as would be known in the art, so long as the external cartridge casing, at least, encloses sample chamber 160 and sensor chip 110.

Still referring to FIG. 1, second cartridge half 150 may further comprise a sensor chip 110, a chip carrier 112, a carrier socket 114, a circuit board 116, and an external connector 180. For example, circuit board 116 may be mounted or form fit inside of second half casing 150 and may be electronically coupled to external connector 180. Circuit board 116 may also support and electronically couple to carrier socket 114, which in turn may support and electronically couple to chip carrier 112. Chip carrier 112 may be configured to physically support and electronically couple to sensor chip 110.

In some examples, sensor chip 110 is a Graphene chip with one or more Graphene transistors, as disclosed herein. The Graphene chip may comprise a plurality of electronic scattering sites located on a top surface of the Graphene chip, wherein each scattering site includes covalently bonded biomarkers that correlate to particular antibodies generated by the human body in reaction to particular infections or diseases (e.g. biomarkers selected for their propensity to bond to antibodies generated by the human body in response to Lyme disease). Further, each scattering site is located on a particular Graphene transistor. The scattering sites are further configured to change the electrical properties of the particular Graphene transistor when the scattering site is exposed to the antibody or antibodies that correlate to the particular bonded biomarker. Accordingly, by applying voltage across the source and drain of each transistor, and properly biasing the source and gate voltage, each Graphene transistor is configured to switch on and/or increase current flow when exposed to a liquid sample containing the antibody or antibodies that correlate to the particular biomarkers bonded to the Graphene transistor's scattering site.

Sensor chip 110 may electrically couple to chip carrier 112. For example, sensor chip 110 may be wire bonded to chip carrier 112. In several embodiments, chip carrier 112 also supports and holds in place sensor chip 110.

Chip carrier 112 may electrically couple to carrier socket 114. In several embodiments, carrier socket 114 supports and holds in place chip carrier 112. Chip carrier 112 may be further configured to snap fit, form fit, or press fit into carrier socket 114 such that electrical leads extending from chip carrier 112 both mechanically and electrically couple to carrier socket 114, but may be mechanically released from carrier socket 114.

Carrier socket 114 may electrically couple to circuit board 116. In several embodiments, circuit board 116 supports and holds in place carrier socket 114. Circuit board 116 may then electrically couple to electrical connector 180. Other electrical and mechanical orientations of sensor chip 110 with respect to circuit board 116 are possible. For example, sensor chip 110 may directly bond to circuit board 116 through a wire bonding, soldering, flip chip solder ball, or other type of electro-mechanical bond as known in the art. In some embodiments, a wire harness or other electric coupling mechanism may facilitate electric coupling of sensor chip 110 with electrical connector 180 such that circuit board 116 is not required.

Still referring to FIG. 1, a biological sample delivery system may be configured to expose sensor chip 110 to a biological sample. The biological sample delivery system may comprise one or more tubes 176, one or more flanges 172 and 174, and sample chamber 160. Flanges 174 and 172 may hydraulically couple to sample chamber 160 through the one or more tubes 176 such that, if a biological sample is introduced through either flange 172 or 174, the biological sample will flow through the tubes 176, into sample chamber 160, and then, if continued pressure is maintained through one of the flanges 172 or 174, the biological sample may be forced out of sample chamber 160 and out of the other flange or flanges 174 or 172. For example, if flanges 174 are input flanges, the flange 172 may act as an exit flange. One of flanges 174 may be used to flush the entire biological sample delivery system with a cleaning solution. Tubes 176 may be hydraulically coupled together with junction 178.

In several examples, sensor chip 110 forms a liquid-tight seal with sample chamber 160. For example, an O-ring 162 may fit within O-ring groove 164 on the outer rim of sample chamber 160, such that when sensor chip 110 is pressed up against sample chamber 160 (e.g. when casing halves 140 and 150 are closed together), O-ring 162 is compressed inside of O-ring groove 164 and against both sample chamber 160 and sensor chip 110, creating a liquid-tight seal.

Figure 2:
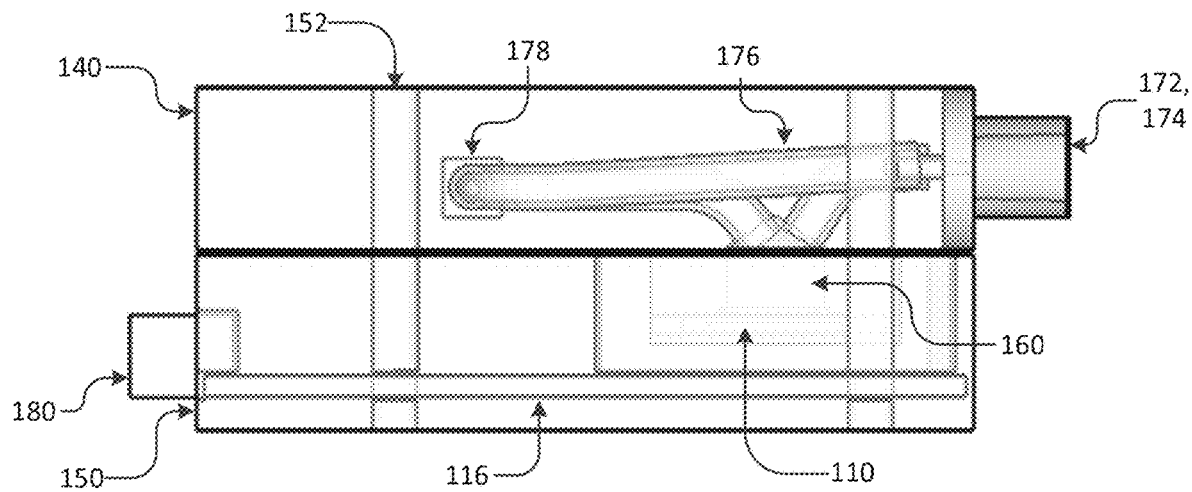
FIG. 2 illustrates a side view of a biological sample analysis device consistent with embodiments disclosed herein.

FIG. 2 illustrates a side view of biological sample analysis device 100. In the non-limiting embodiment illustrated by FIG. 2, casing half 140 is a top half of the casing system and casing half 150 is the bottom half of the casing system. Sample chamber 160 protrudes downward from upper casing half 140 and into bottom casing half 150 when the two halves are configured in the closed position illustrated in FIG. 2. Further, sample chamber 160 is sealed on a bottom side by sensor chip 110 such that, when a biological sample is introduced through flanges 172 and/or 174, it flows through tubes 176, into sample chamber 160, and contacts sensor chip 110.

Figure 3:
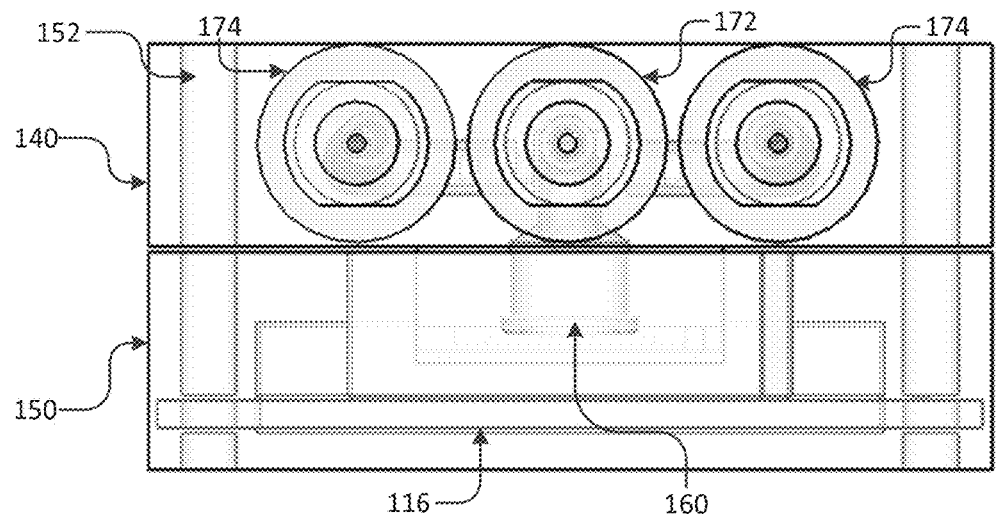
FIG. 3 illustrates a back view of a biological sample analysis device consistent with embodiments disclosed herein.

FIG. 3 illustrates a back view of a biological sample analysis device 100. In the non-limiting example embodiment illustrated by FIG. 3, three sample delivery flanges are located on an external surface of the casing and are configured to hydraulically couple to an external sample deliver system. In some examples, flanges 174 may be input flanges and flange 172 may be an exit flange. For example, one of flanges 174 may be a biological sample input flange, and one of flanges 174 may be a cleaning solution input flange. In other examples, only two flanges may be used, while in some examples, more than three flanges may be used. Other mechanisms for delivering a biological sample to the sensor chip may be used. For example, sensor chip 110 may be dipped in a biological sample stored in a test tube, dewar, cup, catheter bag, or other container. Alternatively, sensor chip 110 may be located within a tube designed to carry the biological sample, or may be configured on a test strip or card and passed directly through the biological sample (e.g. similar to a pregnancy test strip).

Figure 4:
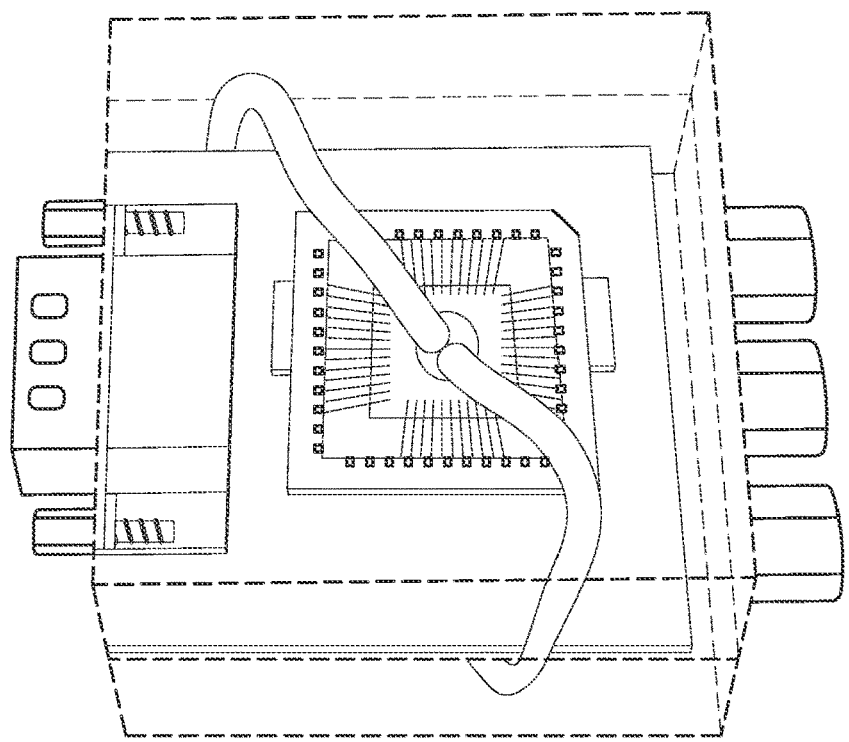
FIG. 4 is a photograph of an example biological sample analysis device consistent with embodiments disclosed herein.

FIG. 4 is a photograph of an example biological sample analysis device. As illustrated by FIG. 4, the casing system may be an acrylic casing or a plastic casing. In other embodiments, the casing system may comprise composite materials, metal, rubber, silicone, glass, resin, or other liquid tight materials as known in the art.

Figure 5:
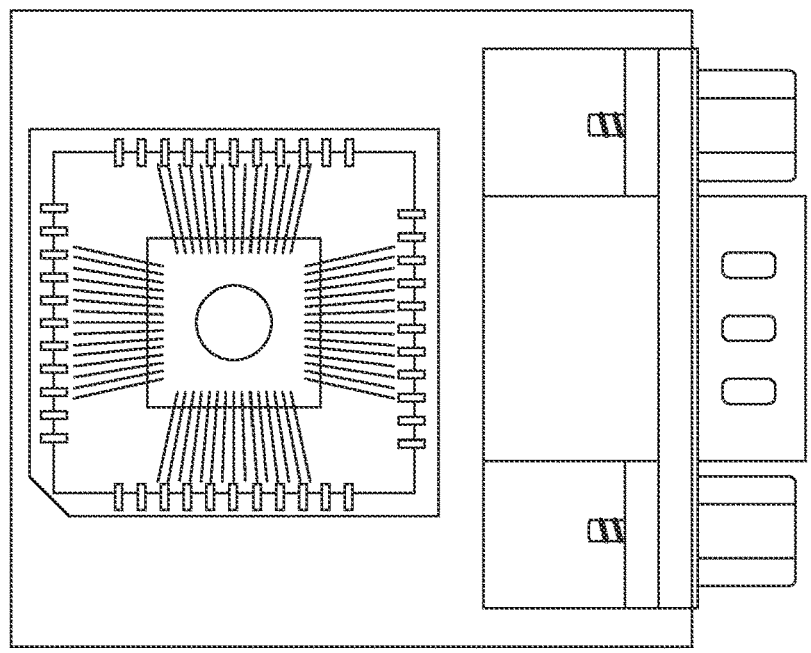
FIG. 5 is a photograph of an electronic biological sample sensor system from an example biological sample analysis device consistent with embodiments disclosed herein.

FIG. 5 is a photograph of an electronic biological sample sensor system from an example biological sample analysis device. As illustrated by FIG. 5, a sensor chip may be wire bonded to a chip carrier, the chip carrier may be coupled to a carrier socket, and the carrier socket may be mounted on a circuit board (e.g. a bread board). The circuit board may then couple to an electronic connector. In some embodiments, the chip carrier is a 44-pin chip carrier. The circuit board may be custom made to electrically couple to the pins from the chip carrier to the connector. In many embodiments, the electronic biological sample sensor system is assembled such that each transistor from the sensor chip completes an electrical circuit through the chip carrier, carrier socket, circuit board, and/or electrical connector. For example, the electrical connector may comprise connector leads for both $V_{DS}$ and $V_{GS}$, to supply drain-source voltage and gate-source bias to each of the transistors on the sensor chip. The electrical connector may further comprise multiple channel leads to monitor and/or measure current flow across each of the transistors independently, such that each channel monitors a different transistor. In some examples, the connector is a sub-D connector.

Figure 6:
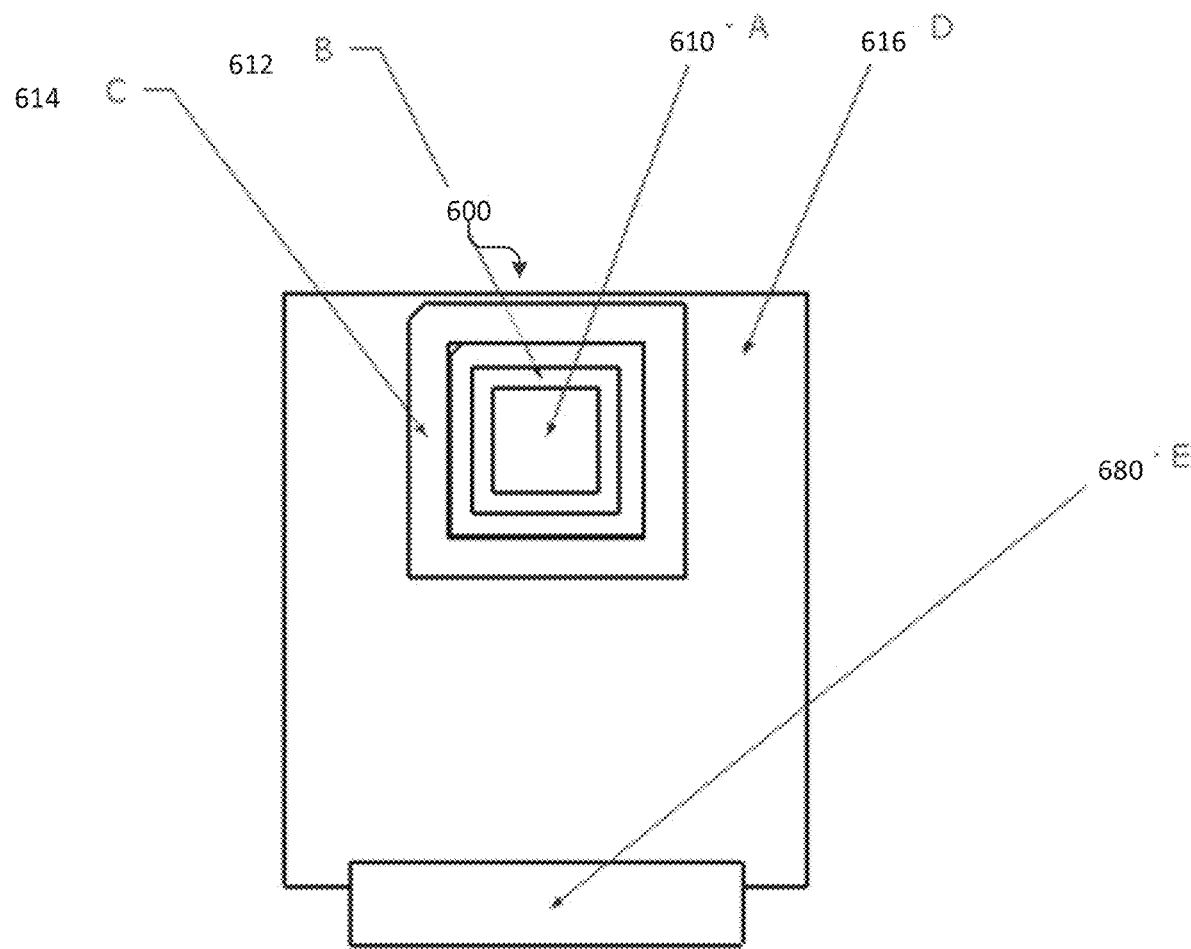
FIG. 6 illustrates a top view of an electronic biological sample sensor system from an example biological sample analysis device consistent with embodiments disclosed herein.

FIG. 6 illustrates a top view of an electronic biological sample sensor system from an example biological sample analysis device. As illustrated, an example electronic biological sample sensor system 600 may comprise sensor chip 610, chip carrier 612, carrier socket 614, circuit board 616, and electrical connector 680. Alternative embodiments may include just sensor chip 610 and electrical connector 680. In some embodiments, an electronic biological sample sensor system is a single integrated circuit comprising one or more Graphene transistors, each transistor being configured to expose the Graphene transistor gates to an external environment (e.g. to a liquid sample resting on a top surface of the Graphene transistor). The electronic biological sample sensor system may further comprise $V_{DS}$ and $V_{GS}$ circuit connections to supply drain-source voltage and gate-source bias to each transistor, as well as at least one electrical channel for monitoring and/or measuring current flow through each transistor.

Figure 7:
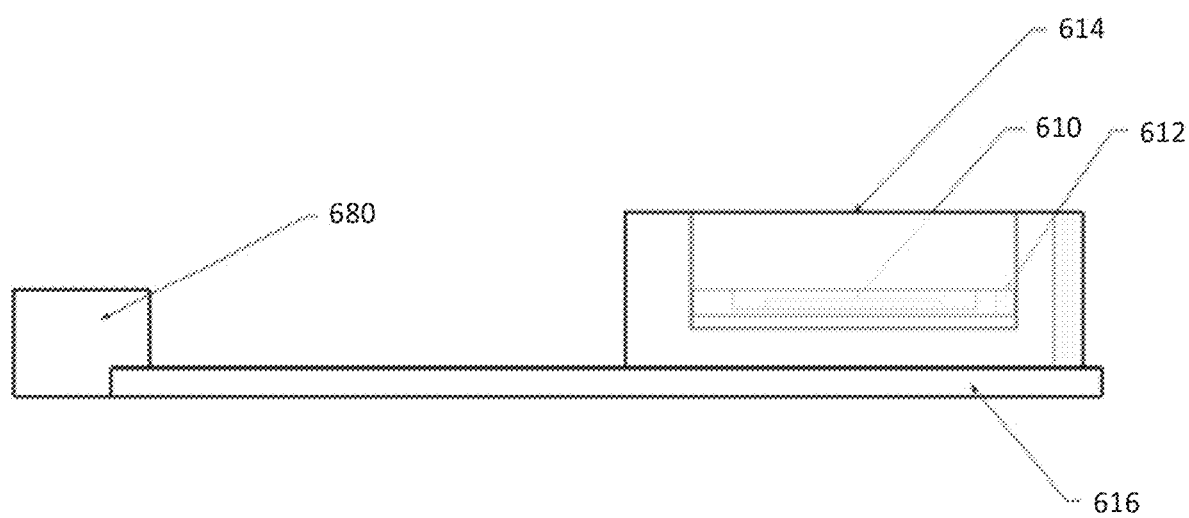
FIG. 7 illustrates a side view of an electronic biological sample sensor system from an example biological sample analysis device consistent with embodiments disclosed herein.

FIG. 7 illustrates a side view of an electronics assembly from an example biological sample analysis device similar to the device illustrated in FIG. 6. Referring to FIG. 7, circuit board 616 may provide electrical connections between electrical connector 680 and sensor chip 610 through chip carrier 612 and carrier socket 614, and may also provide structural support to sensor chip 610, chip carrier 612, and/or carrier socket 614. For example, when sensor chip 610 is bonded to chip carrier 612 and chip carrier 612 is inserted in socket 614, the structural bond between circuit board 616 and carrier socket 612 provides a rigid base for and maintains the structural location of chip carrier 612 and sensor chip 610.

Figure 8:
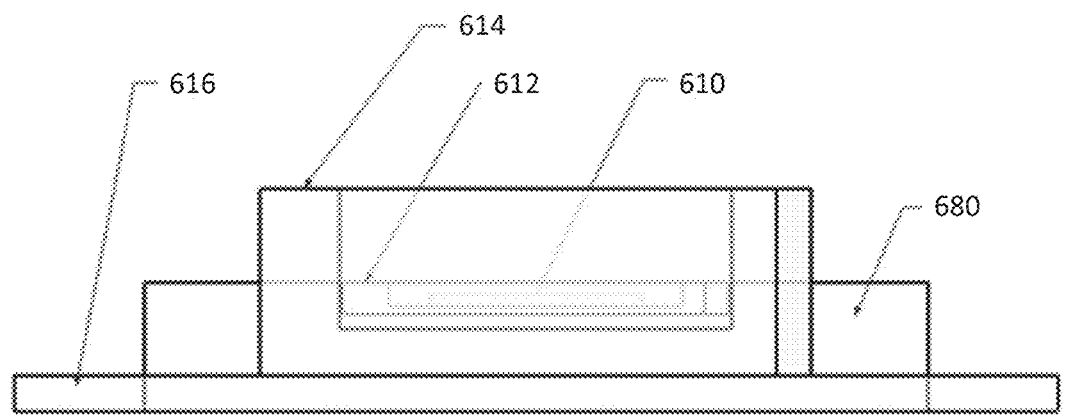
FIG. 8 illustrates a back view of an electronic biological sample sensor system from an example biological sample analysis device consistent with embodiments disclosed herein.

FIG. 8 illustrates a back view of an electronics assembly from an example biological sample analysis device similar to the device illustrated in FIGS. 6 and 7. Referring to FIG. 8, sensor chip 610 may be centrally located with respect to circuit board 616, carrier socket 614, and/or chip carrier 612.

Figure 9:
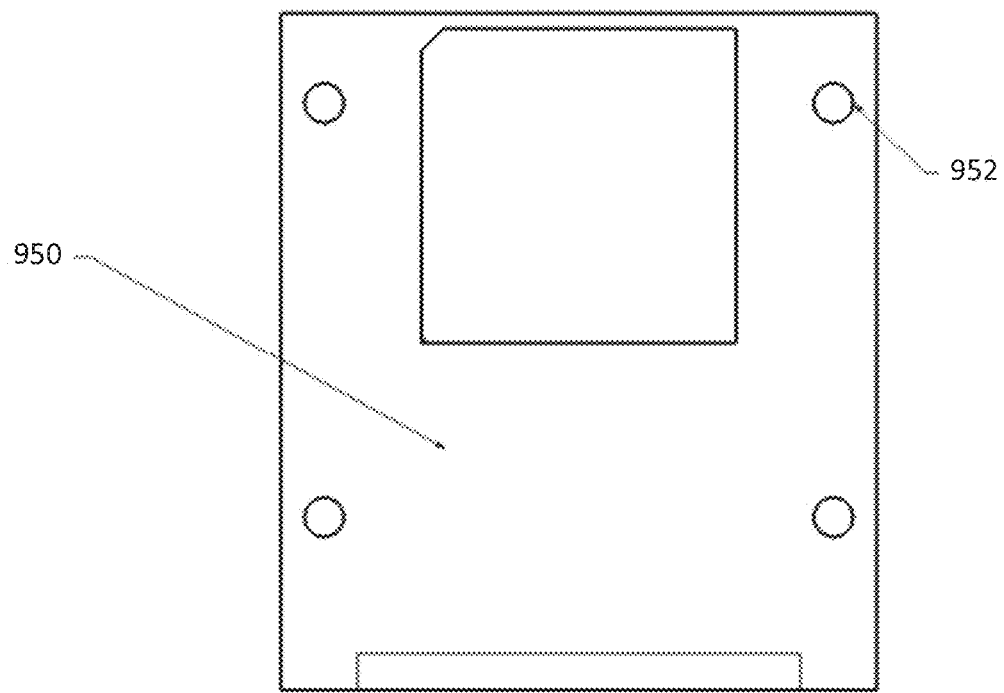
FIG. 9 illustrates a top view of a lower cartridge assembly from an example biological sample analysis device consistent with embodiments disclosed herein.

FIG. 9 illustrates a top view of a lower cartridge assembly from an example biological sample analysis device. Lower cartridge casing 950 may comprise molded or machined plastic, acrylic, glass, ceramic, composite, rubber, metal, or other materials that would be water tight and provide a sterile environment for a biological sample. In some examples, lower cartridge casing 950 comprises thermosetting plastics such as epoxy, polyester or polyurethane or from thermoplastics such as acrylic, polyvinyl chloride or polytetrafluoroethylene (Teflon). Mounting structures 952 may be pins protruding from the casing to mount and align with an upper cartridge assembly, or alternatively, may be holes to accept alignment and/or mounting pins, posts, or screws from the upper cartridge assembly. Other alignment and/or fastening mechanisms may be used to align and secure the upper cartridge assembly with the lower cartridge assembly.

Figure 10:
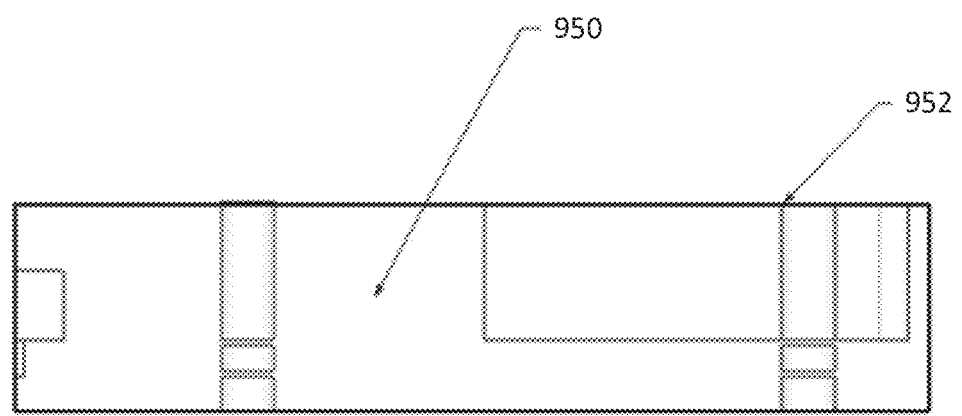
FIG. 10 illustrates a side view of a lower cartridge assembly from an example biological sample analysis device consistent with embodiments disclosed herein.

FIG. 10 illustrates a side view of a lower cartridge assembly from an example biological sample analysis device similar to the device illustrated in FIG. 9. Referring to FIG. 10, example mounting holes 952 may extend vertically through the lower cartridge assembly.

Figure 11:
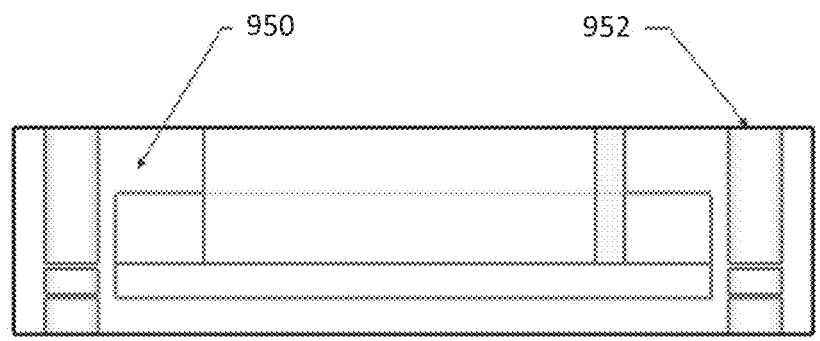
FIG. 11 illustrates a back view of a lower cartridge assembly from an example biological sample analysis device consistent with embodiments disclosed herein.

FIG. 11 illustrates a back view of a lower cartridge assembly from an example biological sample analysis device similar to the device illustrated in FIG. 9. Referring to FIG. 11, openings in casing 950 may be located and configured to accept the electronic biological sample sensor system described in FIGS. 6-8.

Figure 12:
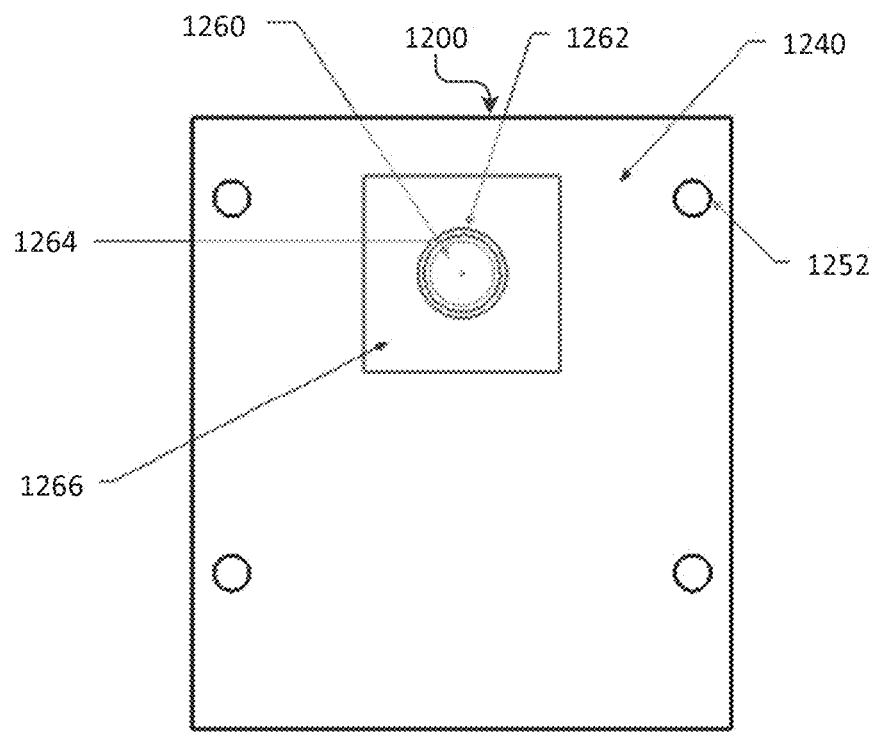
FIG. 12 illustrates an upper view of an upper cartridge assembly from an example biological sample analysis device consistent with embodiments disclosed herein.

FIG. 12 illustrates a top view of an upper cartridge assembly from an example biological sample analysis device. Upper cartridge casing 1240 may comprise molded or machined plastic, acrylic, glass, ceramic, composite, rubber, metal, or other materials that would be water tight and provide a sterile environment for a biological sample. In some examples, upper cartridge casing 950 comprises thermosetting plastics such as epoxy, polyester or polyurethane or from thermoplastics such as acrylic, polyvinyl chloride or polytetrafluoroethylene (Teflon). Mounting structures 1252 may be pins protruding from the casing to mount and align with the lower cartridge assembly, or alternatively, may be holes to accept alignment and/or mounting pins, posts, or screws from the lower cartridge assembly. Other alignment and/or fastening mechanisms may be used to align and secure the upper cartridge assembly with the lower cartridge assembly.

Still referring to FIG. 12, upper cartridge assembly may further comprise biological sample chamber 1260, O-ring groove 1262, O-ring 1264, and/or cartridge body alignment tab 1266. For example, sample chamber 1260 may be configured to hold a liquid biological sample when sealed on a bottom side by the sensor chip from the electronic biological sensor system. O-ring 1264 may be located inside O-ring groove 1262 and configured to form a seal between sample chamber 1260 and the sensor chip when the upper and lower cartridge assemblies are secured together. Cartridge body alignment tab 1266 is shaped to fit inside a similarly shaped socket on the lower cartridge assembly to align the upper and lower cartridge assemblies.

Figure 13A:
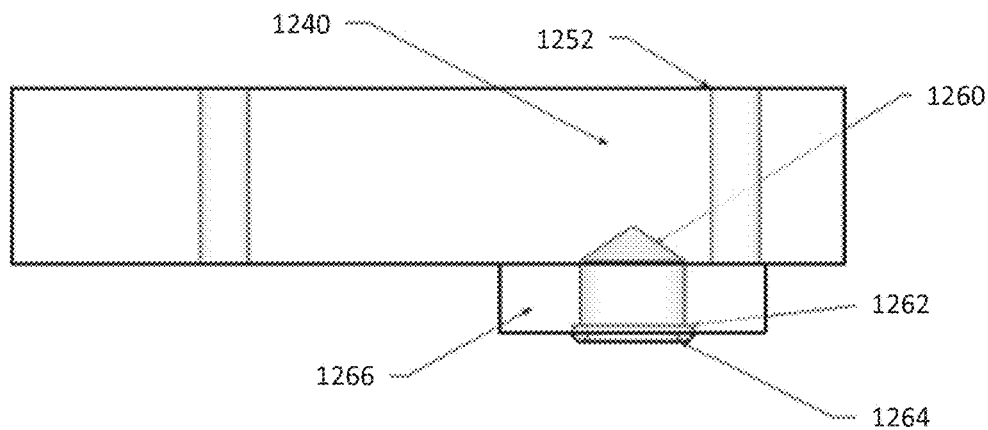
FIG. 13A illustrates a side view of an upper cartridge assembly from an example biological sample analysis device consistent with embodiments disclosed herein.

FIG. 13A illustrates a side view of an upper cartridge assembly from an example biological sample analysis device similar to the device illustrated in FIG. 12. Referring to FIG. 13A, sample chamber 1260 and cartridge body alignment tab 1266 may protrude downward from the upper cartridge assembly.

Figure 13B:
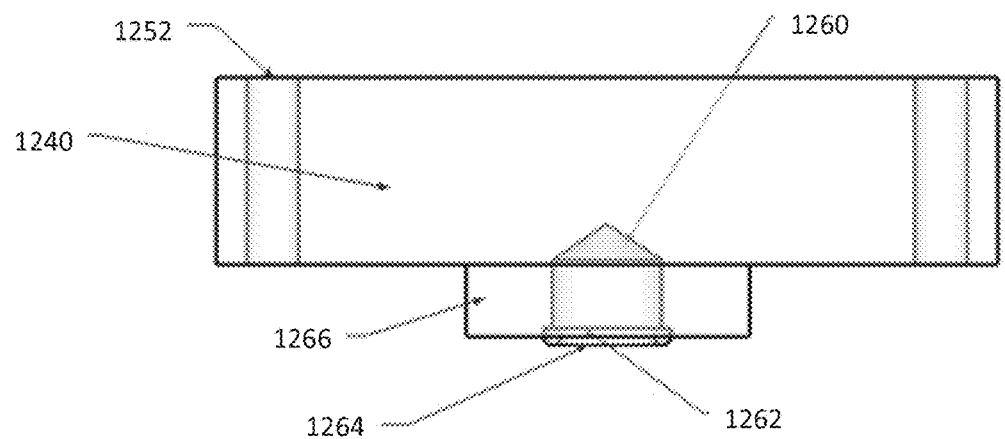
FIG. 13B illustrates a back view of an upper cartridge assembly from an example biological sample analysis device consistent with embodiments disclosed herein.

FIG. 13B illustrates a back view of a top cartridge assembly from an example biological sample analysis device similar to the device illustrated in FIGS. 12 and 13A. Referring to FIG. 13B, sample chamber 1260 and cartridge body alignment tab 1266 may be centrally located within the upper cartridge assembly.

Figure 14A:
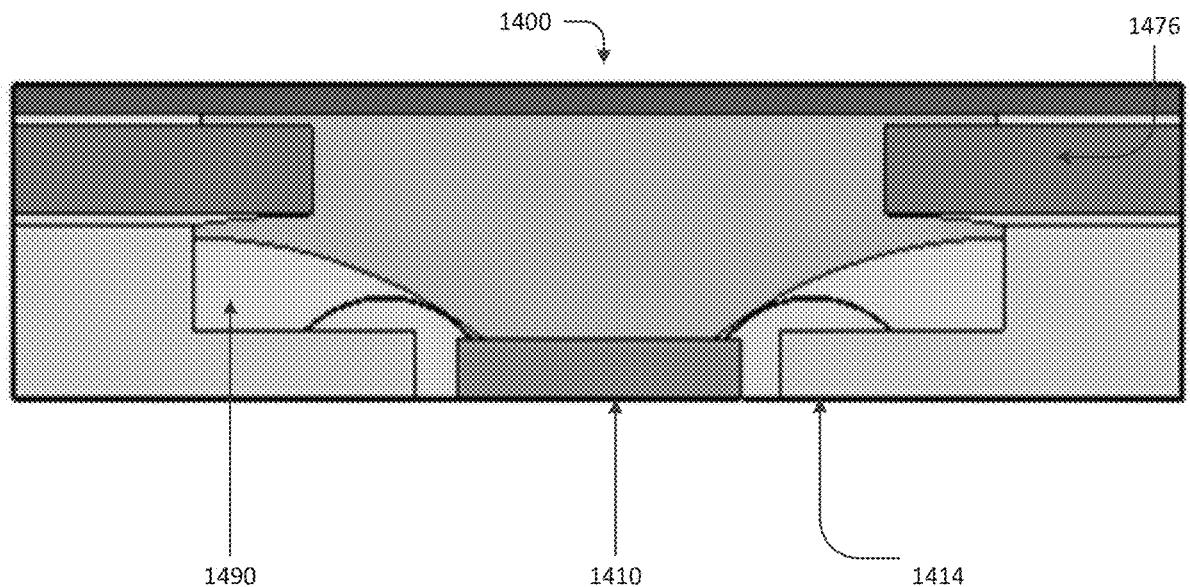
FIG. 14A illustrates a side view of a sample chamber from an example biological sample analysis device consistent with embodiments disclosed herein.
Figure 14B:
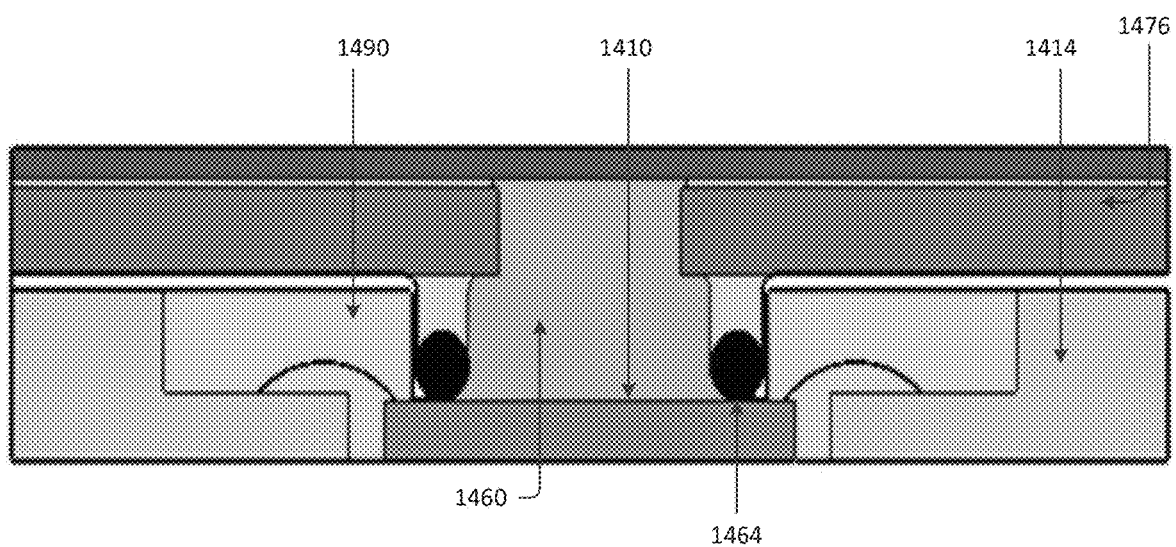
FIG. 14B illustrates a side view of a sample chamber from an example biological sample analysis device including an O-ring used to form a liquid-tight and sterile seal consistent with embodiments disclosed herein.

FIG. 14A illustrates a side view of a sample chamber epoxied or molded onto a chip carrier from an example biological sample analysis device clamped to a sensor chip from an example biological sample analysis device. Referring to FIG. 14A, sample chamber 1400 comprises a molded solid material (e.g. molded plastic) 1490 configured to hold a liquid biological sample. Sensor chip 1410 is located on a lower side of sample chamber 1400 to complete a seal such that, if a liquid biological sample is placed in the sample chamber, gravity will cause the liquid biological sample to contact a top surface of sensor chip 1410. Sensor chip 1410 may be secured in sample chamber 1400 using epoxy, molded plastic, or another moldable or formable solid material that may be configured to form a liquid-tight and sterile seal with sensor chip 1410. FIG. 14B illustrates the side view of a sample chamber similar to FIG. 14A that further illustrates a sensor chip 1410 that may also be forced or clamped against O-ring 1464 to form a liquid-tight and sterile seal. As illustrated by FIG. 14B, tubing 1476 may be configured to deliver a liquid biological sample into sample chamber 1400.

Figure 15:
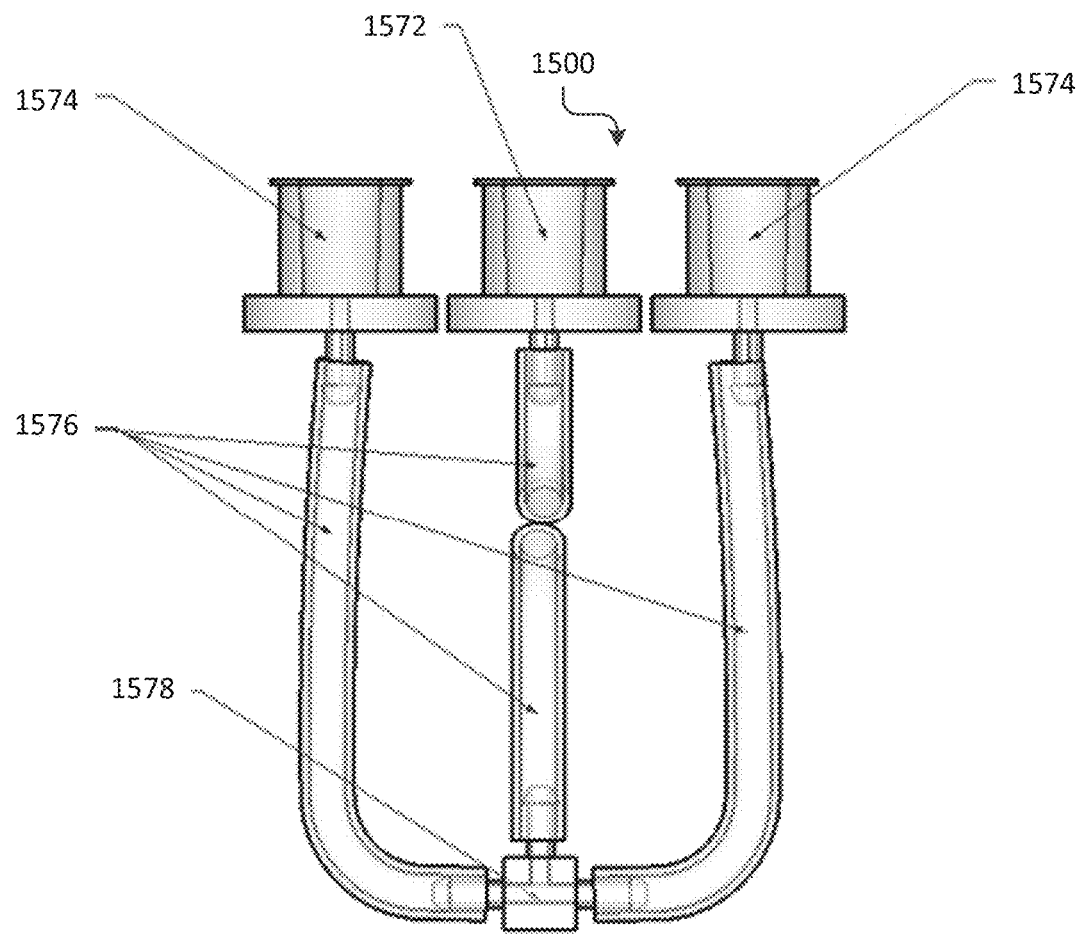
FIG. 15 illustrates a top view of a liquid handling assembly from an example biological sample analysis device consistent with embodiments disclosed herein.

FIG. 15 illustrates a top view of a liquid handling assembly from an example biological sample analysis device. Liquid handling assembly 1500 may comprise one or more tubes 1576 and one or more flanges 1572 and 1574. Flanges 1572 and 1574 are configured to hydraulically connect liquid handling assembly 1500 to an external liquid source. For example, flanges 1574 may accept input from a liquid biological sample source and/or a cleaning source to enable flushing of the liquid handling system with a cleaning solution (e.g. saline). Flange 1572 may be a liquid exhaust flange to enable liquid handling system 1500 to exhaust the biological sample or cleaning solution. Flanges 1572 and 1574 may be Luer fittings, for example. Tubes 1576 may be hydraulically coupled with one or more junction connectors 1578. Liquid handling assembly 1500, and biological sample chamber 1260 illustrated in FIGS. 12-14, may be cleaned with a cleaning solution and/or with steam or chemical sterilization (e.g. bleach, ozone, or hydrogen peroxide).

Figure 16A:
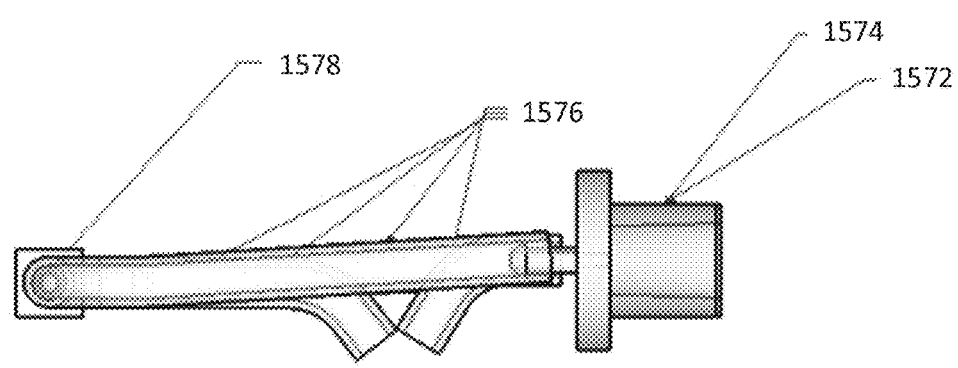
FIG. 16A illustrates a side view of a liquid handling assembly from an example biological sample analysis device consistent with embodiments disclosed herein.
Figure 16B:
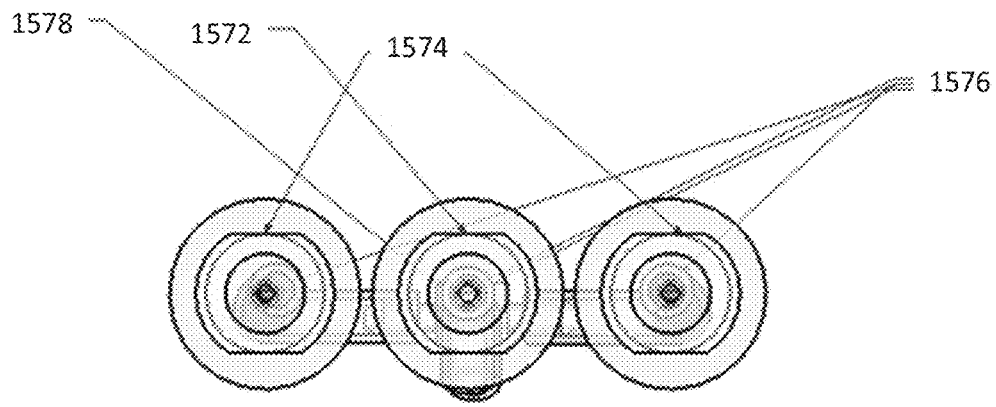
FIG. 16B illustrates a front view of a liquid handling assembly from an example biological sample analysis device consistent with embodiments disclosed herein.

FIG. 16A illustrates a side view and FIG. 16B illustrates a front view of a liquid handling assembly from an example biological sample analysis device from an example biological sample analysis device similar to the liquid handling assembly illustrated in FIG. 15. As illustrated, tube 1576 may couple to flanges 1574 and 1572 with a liquid-tight coupling mechanism such as a burr or form fit coupling. Tubes 1576 also bend downward to deliver a liquid biological sample into the sample chamber.

Figure 17A:
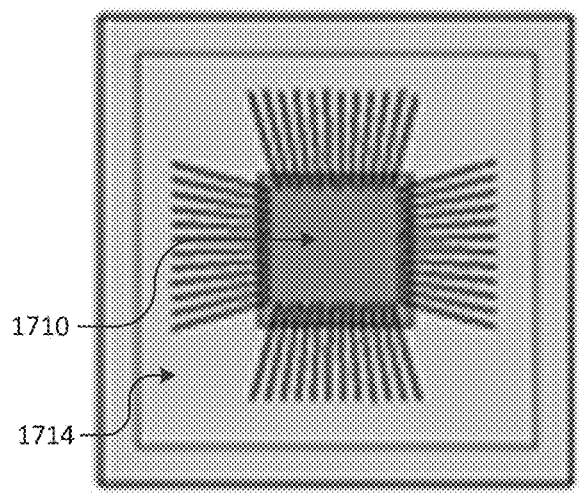
FIG. 17A illustrates a top view of an example biological sample analysis sensor chip wirebonded in a chip carrier consistent with embodiments disclosed herein.
Figure 17B:
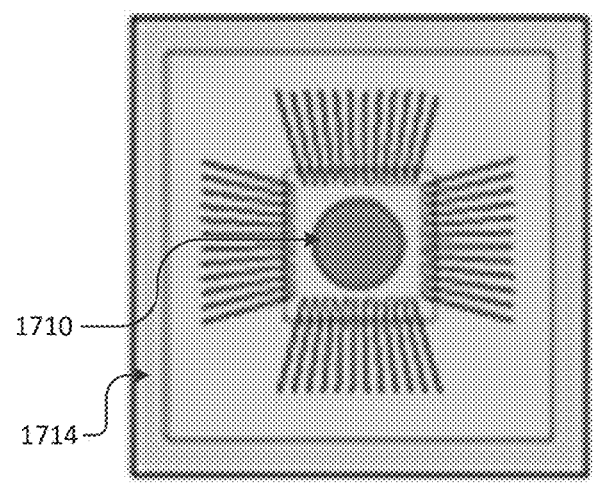
FIG. 17B illustrates a top view of an example biological sample analysis sensor chip covered with a molded plastic cover shaped to form a sample chamber consistent with embodiments disclosed herein.
Figure 17C:
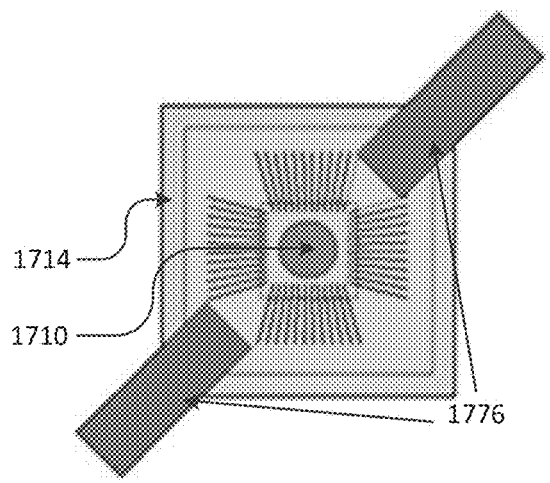
FIG. 17C illustrates a top view of an example biological sample analysis sensor chip covered by a sample chamber that is hydraulically coupled to sample deliver tubing consistent with embodiments disclosed herein.
Figure 17D:
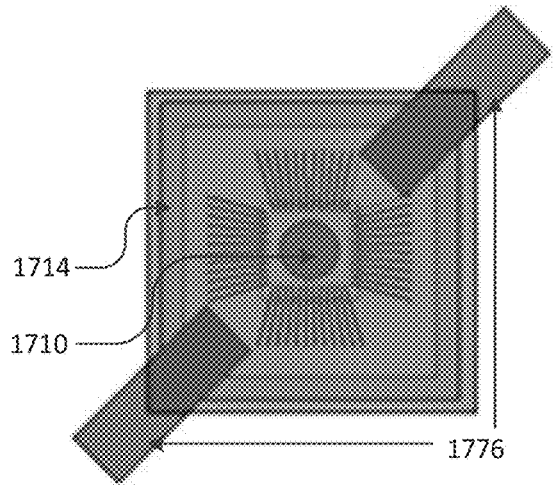
FIG. 17D illustrates a top view of an example biological sample analysis sensor chip covered by a sample chamber and encased in an external casing consistent with embodiments disclosed herein.

FIG. 17A illustrates a top view of an example biological sample analysis sensor chip wirebonded in a chip carrier from an electronic biological sensor system. Sensor chip 1710 may be a Graphene chip with a plurality of Graphene transistors wherein each transistor electrically couples through wire leads to chip carrier 1714. FIG. 17B illustrates a top view of sensor chip 1710 covered with a molded plastic cover shaped to form a sample chamber similar to sample chamber 1400 illustrated in FIGS. 14A and 14B. Accordingly, when a liquid biological sample is introduced into the sample chamber, gravity will cause the biological sample to contact sensor chip 1710. FIG. 17C illustrates a top view of sensor chip 1710, covered with a sample chamber, and hydraulically coupled to tubes 1776 configured to deliver a liquid biological sample into sample chamber 1400. FIG. 17D illustrates a top view sensor chip 1710 covered by a sample chamber and encased in an external casing similar to external casings disclosed in FIGS. 1-4 and 6-14.

Figure 18:
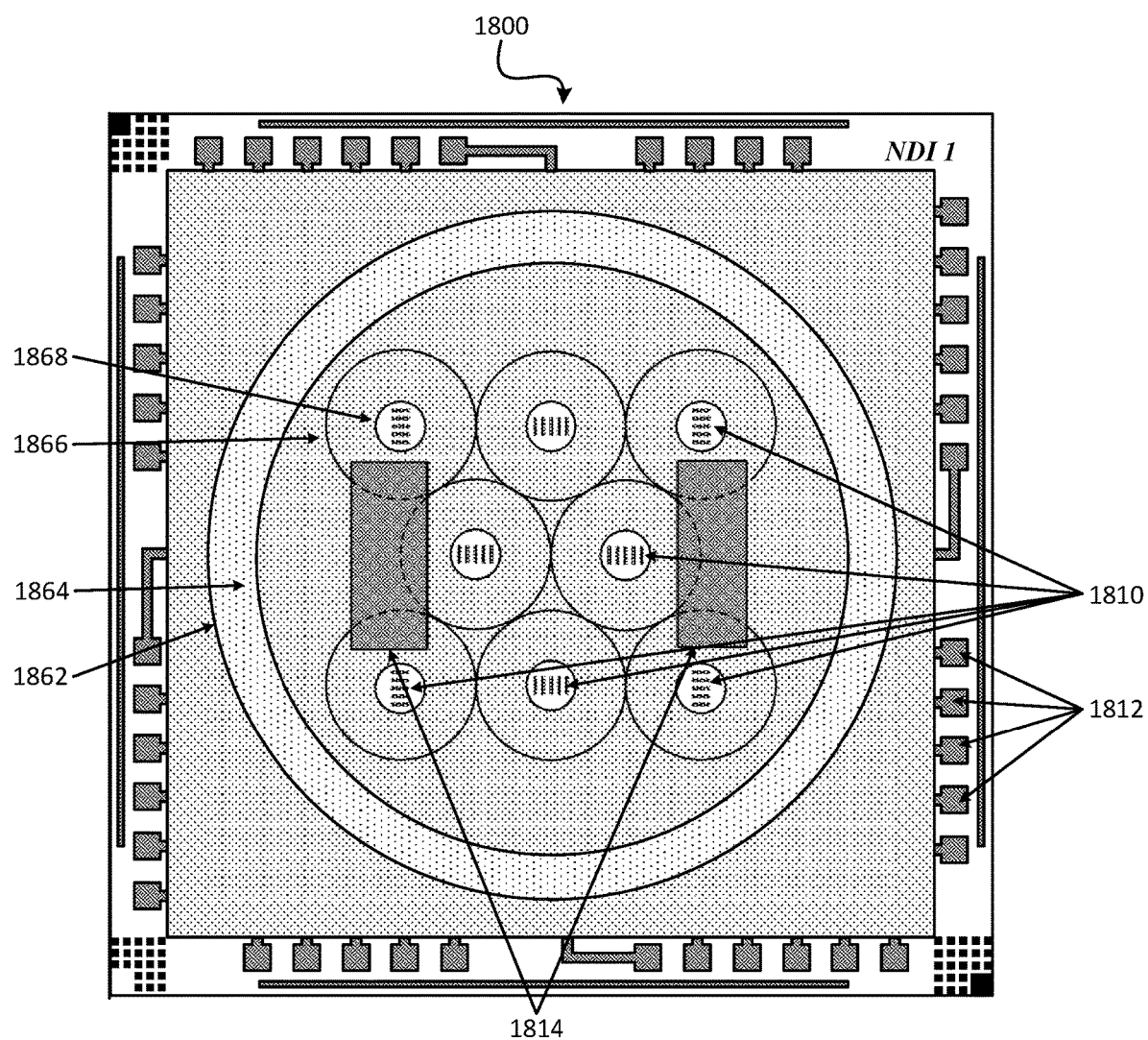
FIG. 18 illustrates a top view of an example biological sample analysis sensor chip consistent with embodiments disclosed herein.

FIG. 18 illustrates a top view of an example biological sample analysis sensor chip as used in an electronic biological sample sensor system. For example, biological sample analysis sensor chip 1800 may comprise one or more transistors 1810. Each transistor 1810 may comprise Graphene. For example, each transistor 1810 may comprise $sp^2$ hybridized Carbon ($Csp^2$) that is a single atomic layer thick, or just a few atomic layers thick. Each Graphene transistor 1810 may further comprise one or more electronic scattering sites, wherein each electronic scattering site comprises Carbon that is $sp^3$ hybridized. $Sp^3$ hybridized Carbon enables covalent bonding with a biomolecule at the $Csp^3$ orbital. The covalently bonded molecules may act as biomarkers wherein predetermined biomarkers will additionally bond to predetermined antibodies generated by a living organism (e.g. a human or a mammal) in response to a particular virus, bacteria, disease, or illness. For example, the Graphene chip may be prepared for chemical functionalization by chemical oxidation with Diazonium salts, Sulfuric Acid, Potassium Permanganate or Hydrogen Peroxide. Antibody attachment may start by linking Carboxylic Acid groups on the Graphene to amine groups on the antibody or linker using 1-Ethyl-3-(3-Dimethylaminopropyl)Carbodiimide (EDC) and N-Hydroxysuccinimide (NETS). A linker molecule may be used when direct attachment to the antibody is not possible. In one example, Streptavidin is used to bind a Biotinylated protein or Nitrotriacetic Acid is used to bind a His-tagged protein. Multiple antibodies can be attached to a single chip by limiting the reaction volume to sufficiently a small shot on top of a group of transistors.

In several embodiments, the Graphene sensor chip may be constructed using a photolithography fabrication process to form Graphene transistors connected to metal contact leads. For example, the Graphene may be a CVD Graphene on a plastic film that is placed on a wafer (e.g. a silicon wafer) and exposed to a solvent (e.g. acetone) to dissolve the plastic and leaving the Graphene on the wafer. The Graphene may then be rinsed (e.g. with isopropyl alcohol, methanol, and/or water) and heated to remove residue. In some examples, the wafer with the Graphene layer is heated for between 30 minutes and four hours. If a shorter time is used, than the wafer with the Graphene layer may be exposed to heat of between 150 degrees C. to 300 degrees C., whereas if a longer heating time is selected, than the wafer with the Graphene layer may be exposed to air at room temperature. Other methods of depositing Graphene on a wafer are possible, including standard material deposition processes as would be known in the art.

One example method for constructing a Graphene sensor chip includes depositing alignment marks and some wiring on a wafer using photolithography, depositing a Graphene layer, and then depositing final wiring using photolithography. Another example method for constructing a Graphene sensor chip includes depositing Graphene and depositing all wiring in a single step. The steps described are non-limiting and may be performed in any order. After the deposition of the Graphene and wires, many examples include dicing the wafers into chips, bonding the chips into chip carriers, and loading the chips onto circuit boards. Several examples further include electrically coupling a socket for the chips to an external electrical connector. In some examples, the bonding of the chip to the chip carrier is a wire bonding process. In some examples, the chip carrier is a 44-pin ceramic or plastic chip carrier, but other chip carrier formats are possible as would be known in the art.

In some examples, the circuit boards are configured such that at least two pins are voltage inputs and the remaining pins are measurement channels. For example, one voltage input may be used to set the drain-source bias on the Graphene transistors ($V_{DS}$) and the other voltage input may be used to set the gate-source bias on the Graphene transistors ($V_{GS}$). The $V_{DS}$ lead may electrically couple to the drain electrode on each Graphene transistor, and the $V_{GS}$ lead may electrically couple to the gate and/or source electrodes of each Graphene transistor and may be used to set the gate/source bias. Measurement channel leads may then electrically couple to individual Graphene transistors to measure current when the Graphene transistor is exposed to a liquid sample. For example, when biomarkers bonded to the Graphene transistor gate are selected for their bonding properties with specific antibodies. When a specific biomarker bonds with the specific antibody, the conductive properties of the Graphene change, causing that particular transistor to switch on, and allowing current to flow to the transistor's source and respective measurement channel. Graphene transistors on any given sensor chip may be configured with a uniform biomarker designed to bond with a uniform antibody (e.g. an antibody for Lyme disease), or multiple biomarkers may be used for the different Graphene transistors, such that a single sensor chip may detect multiple antibodies present in a single liquid sample.

Any biomarker that is known to bond to a particular antibody may be used in the sensor chip to detect the presence of that antibody. The following non-limiting list includes several example diseases and infections with known antibody-to-biomarker relationships:

Autoimmune diseases
  Hashimoto's thyroiditis
  Hyperthyroidism
  Multiple sclerosis
  Rheumatoid arthritis
Bacterial infections
  *Bacillus anthracis* (anthrax)
  *Escherichia coli* (food poisoning)
  *Haemophilus influenzae* (bacterial influenza)
  *Neisseria gonorrhoeae* (gonorrhea)
  *Neisseria meningitides* (meningitis)
  *Plasmodium* (malaria)
  *Rickettsia prowazekii* (typhus)
  *Salmonella enterica* (food poisoning, typhoid)
  *Staphylococcus* (food poisoning, staph)
  *Streptococcus pneumonia* (pneumonia)
  *Treponema pallidum* (syphilis)
Viral infections
  Ebola
  Epsein-Bar virus
  Hepatitis A, B, C, D, E
  Herpes simplex virus (cold sore, herpes)
  Herpes zoster (chickenpox, shingles)
  HIV
  Human coronavirus (common cold)
  Influenza (common cold)
  Norovirus
  Rhinovirus (common cold)
  Rotavirus
  SARS coronavirus
  Variola virus (smallpox)
Cancer Markers
  Alpha fetoprotein
  beta-2-microglobulin
  beta-human chorionic gonadotropin
  Calcitonin
  Cancer antigen 123
  Cancer antigen 125
  Cancer antigen 15-3
  Cancer antigen 19-9
  Cancer antigen 27.29
  Carcinoembryonic antigen
  Chromogranin A
  Cytokeratin
  Human chorionic gonadotropin
  Osteopontin
  Prostate specific antigen Still referring to FIG. 18, transistors 1810 may be organized and/or located within wells 1868 to concentrate a biological sample over the transistors. Wells 1868 may be formed with well structure 1866 that may comprise capillary tubing plastic, rubber, composite, silicon, or other structural materials as known in the art. Each well 1868 may include one or more transistors 1810, and each sensor chip 1800 may include one or more wells 1868, wherein each well may include a homogeneous biomolecule for detection of a particular antibody. In some examples, wells on the same sensor chip may include different biomolecules such that a single sensor chip may be configured to detect a plurality of antibodies. All of the transistors 1810 and wells 1868 make up an antibody detection surface on sensor chip 1800. As illustrated by FIG. 18, the antibody detection surface may be enclosed within O-ring 1864 and configured to be sealed within a sample chamber with a liquid-tight seal. Bond pads, or leads 1812 electrically couple to the transistors or to reference electrodes 1814 and allow the sensor chip to electrically couple to a chip carrier, carrier socket, circuit board, and/or external electrical connector.

Figure 19:
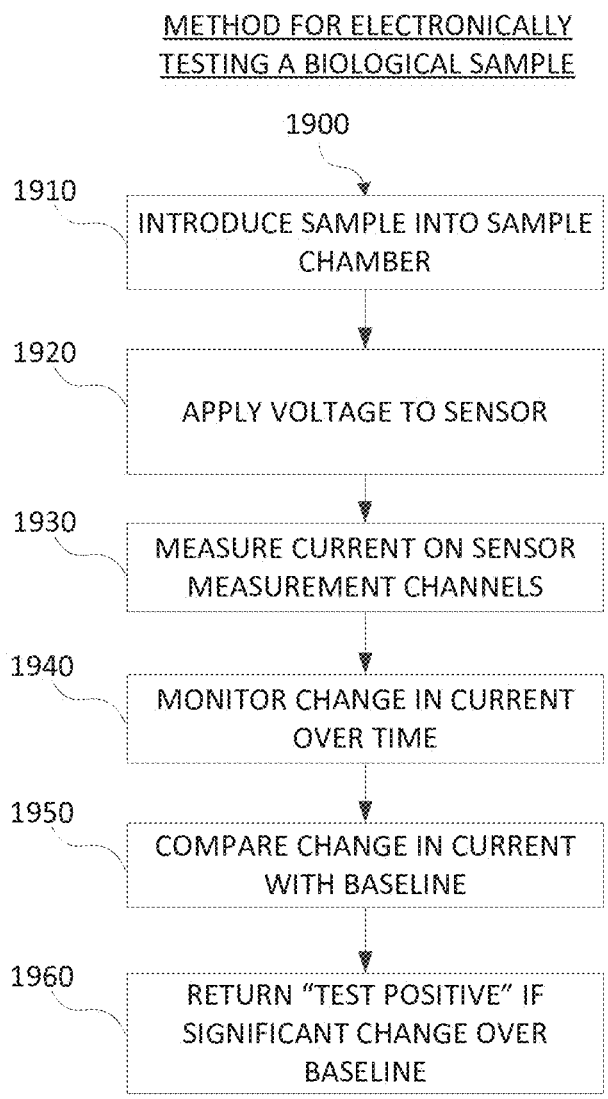
FIG. 19 is a process diagram illustrating a method for electronically testing a biological sample consistent with embodiments disclosed herein.

FIG. 19 is a process diagram illustrating a method for electronically testing a biological sample (e.g. using a biological sample analysis device). A method for electronically testing a biological sample 1900 may include introducing a biological sample into a sample chamber at step 1910. For example, the biological sample may be urine or blood and the sample chamber may be a biological sample chamber and sensor chip similar to embodiments disclosed in FIGS. 1-18. Method 1900 may further include applying a voltage to the sensor chip at step 1920. For example, a voltage may be applied to connector leads electronically coupled to transistors within the sensor chip to supply a drain-source voltage and a gate-source bias. Method 1900 may further include measuring current on sensor measurement channels at step 1930. For example, each sensor measurement channel may be monitored through connector leads electronically coupled to corresponding transistors. Method 1900 may further include monitoring a change in current over time at step 1940, and comparing the change in current with a baseline measurement at step 1950 (e.g. a current measurement taken when the sensor chip was exposed to only saline or another control liquid). Method 1900 may further include returning a "test positive" signal at step 1960 if a threshold change in current over baseline is reached, indicating the presence of an antibody-biomolecule bond at one or more scattering sites as disclosed in FIG. 18.

The steps of measuring current on sensor measurement channels 1930, monitoring changes in current over time 1940, comparing the changes with a baseline measurement 1950, and returning a "test positive" signal may be performed by an electronic biological sample testing module. For example, a biological sample testing module may be a computer module as disclosed in FIG. 25 that includes a processor programmed with one or more computer programs configured to perform the steps disclosed herein. Other steps of method 1900 may be similarly performed by a computer module.

Figure 20:
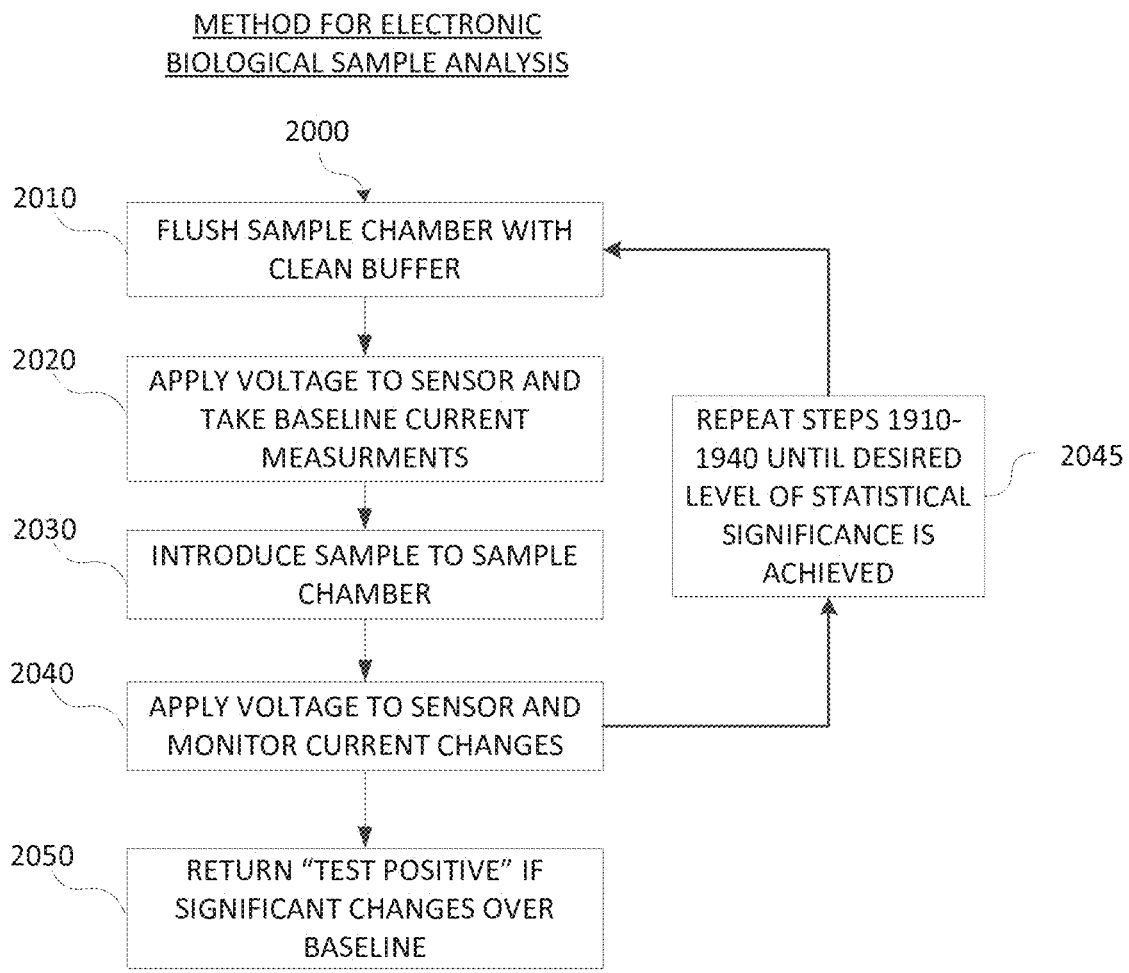
FIG. 20 is a process diagram illustrating a method for electronic biological sample analysis consistent with embodiments disclosed herein.

FIG. 20 is a process diagram illustrating a method for electronic biological sample analysis. A method for electronic biological sample analysis 2000 includes flushing a sample chamber with a clean buffer at step 2010. For example, the sample chamber may be a biological sample chamber similar to embodiments disclosed herein and the clean buffer may be a saline solution or other sterile solution as known in the art. Method 2000 further includes applying voltage to an electronic biological sample sensor system at step 2020. For example, voltage may be applied across the source-drain and source-gate of transistors in a sensor chip. Method 2000 further includes introducing a sample to the sample chamber at step 2030, applying a voltage to the sensor, and monitoring current changes at step 2030. The applied voltage will cause current to vary from a baseline if the biological sample includes antibodies that correspond to biomolecules bonded to scattering sites in the sensor chip transistors. Steps 1910 through 1940 may be repeated multiple times at step 2045 to increase statistical significance of the measurements. Method 2000 may further include returning a "test positive" signal at step 2050 if the average change in current over baseline exceeds a predetermined threshold level. The steps disclosed in method 2000 may be performed by an electronic biological sample testing module. For example, a biological sample testing module may be a computer module as disclosed in FIG. 25 that includes a processor programmed with one or more computer programs configured to perform the steps disclosed herein.

In some examples, all of the applied and measured voltages are referenced to a common ground. A single device measurement may include applying a voltage (e.g between 0.1V and 1V) to the drain of all of the Graphene transistors ($V_{DS}$) and a voltage (e.g between -1V and 1V) to the liquid in the sensing chamber ($V_{GS}$). The resulting liquid voltage ($V_{REF}$) can be monitored through a reference electrode 1814. The electrical baseline of each of the sensors on the chip can be measured by recording the current on all of the sensor measurement channels when $V_{REF}$ is 0V. $V_{GS}$ can be controlled such that if $V_{REF}$ changes up or down (e.g in a range from -1V to 1V) while holding $V_{DS}$ steady. The current can be measured on all of the sensor measurement channels. For each measurement channel, the resulting data, when considered with a Y-axis of current and an X-axis $V_{REF}$, can be fitted with a line. The slope and X-axis intercept of the line can be calculated where the electrical baseline current, slope, and intercept of the fit line form three data points in a measurement vector for each sensor in a device measurement. To increase statistical significance, a device measurement can be repeated multiple times (e.g. 3 to 5 times) to obtain an average value and statistical variance for the measurement vector for each sensor. This process can be automated using a computer module as disclosed herein.

In some examples, a method for electronic biological sample analysis includes connecting a system for electronic biological sample analysis to an electrical system, flushing the system for electronic biological sample analysis with clean serum or buffer, and measuring a baseline device measurement to obtain a baseline set of measurement vectors. The method may further include injecting a biological sample into the system and measuring a device measurement at regular intervals over an incubation period (e.g. every minute for 10, 20, or 30 minutes). The method may further include flushing the system with clean serum or buffer and measuring a device measurement at a regular interval (e.g. every minute for 1, 5, or 10 minutes). The system may then be flushed with clean serum or buffer again and repeating measuring a device measurement at a regular interval. The method may further include comparing the measurement vectors before, during, and after exposing the system to the biological sample and analyzing the date for a significant change in the measurement vector for many similarly functionalized sensors indicating a binding event, which can be reported as a positive identification.

Figure 21:
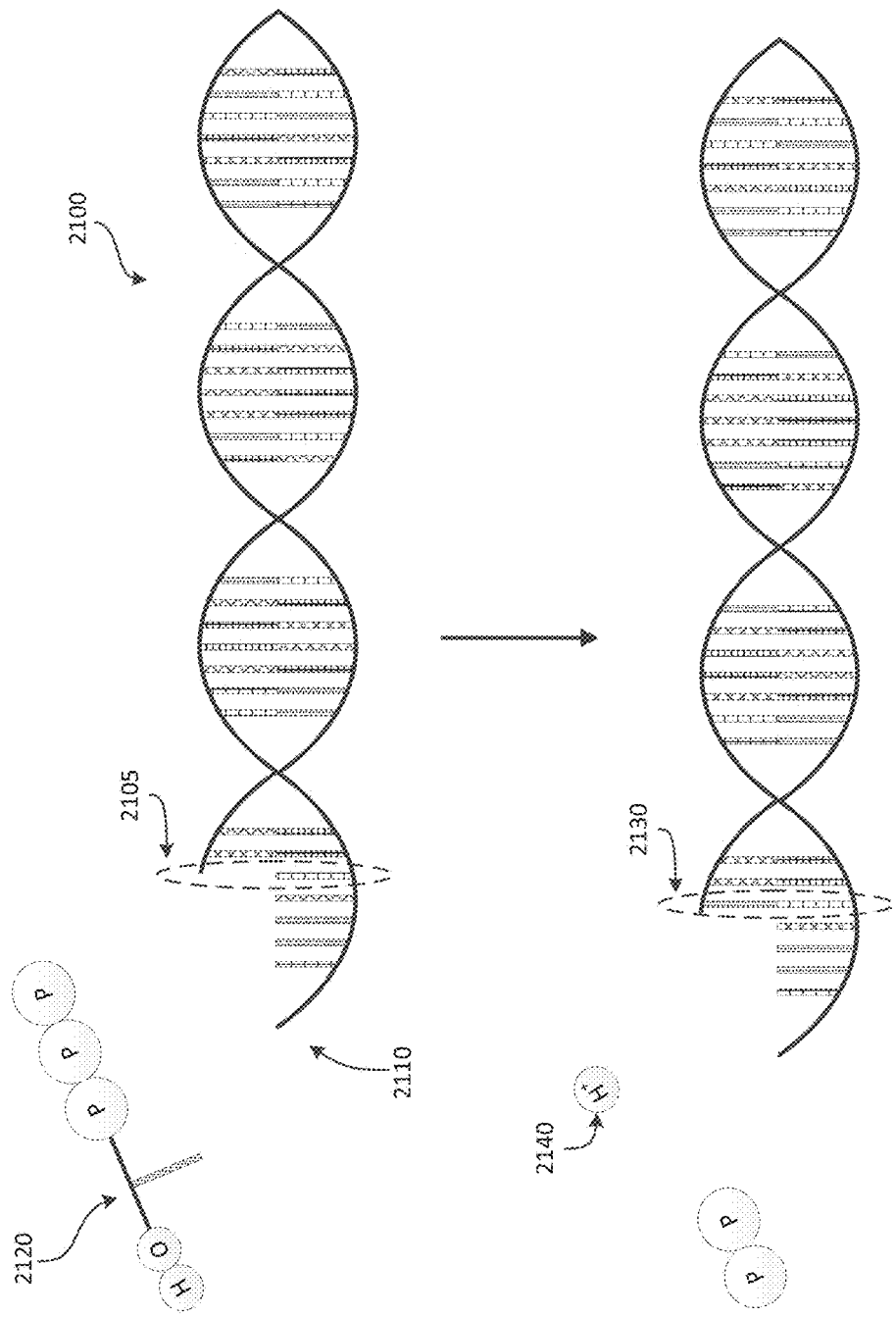
FIG. 21 is an example diagram illustrating the process of binding of subjugate bases of DNA.

The technology of the present disclosure is applicable to not only infection and disease detection, but for other analysis as well. One such type of analysis is DNA sequencing. When subjugate bases of DNA (or RNA) bind, the binding process releases ions into the surrounding suspension. FIG. 21 illustrates an example of the binding process. As illustrated, a DNA chain 2100 is shown with subjugate base pairs. At one end 2110, only one side of the double helix formation is present, with unpaired bases. Binding occurs in the presence of a sequencing probe 2120—shown in FIG. 21 as deoxyribose nucleoside triphosphate (dNTP). A sequencing probe is a fragment of DNA (or RNA in the sequencing of DNA) used to detect the presence of nucleotide sequences that are complimentary to the sequence of the sequencing probe. If the dNTP compliments the next exposed base (illustrated in area 2105), binding occurs and a subjugate base pair is created (illustrated in area 2130). The release of a hydrogen ion results in a change in the local pH of the suspension. By knowing the dNTP being introduced into the suspension, it is possible to determine which base—adenine, thymine, guanine, or cytosine—was exposed and the precise structure of the strand. If a chain of the same exposed base is present (i.e., more than one of the same base is found consecutively on a single-strand of the DNA molecule), more ions will be released, resulting in a greater change in the pH of the suspension. By measuring the change in the electrical properties of transistors caused by changes in pH, it is possible to identify the DNA sequence present in the suspension. Some current DNA sequencing tools employ a silicon transistor pH meter, such as ion-sensitive field-effect transistor (ISFET), to identify changes in the local pH level indicative of DNA binding. The biological sample analysis sensor chip discussed above is exceptionally suited for such DNA testing.

Figure 22:
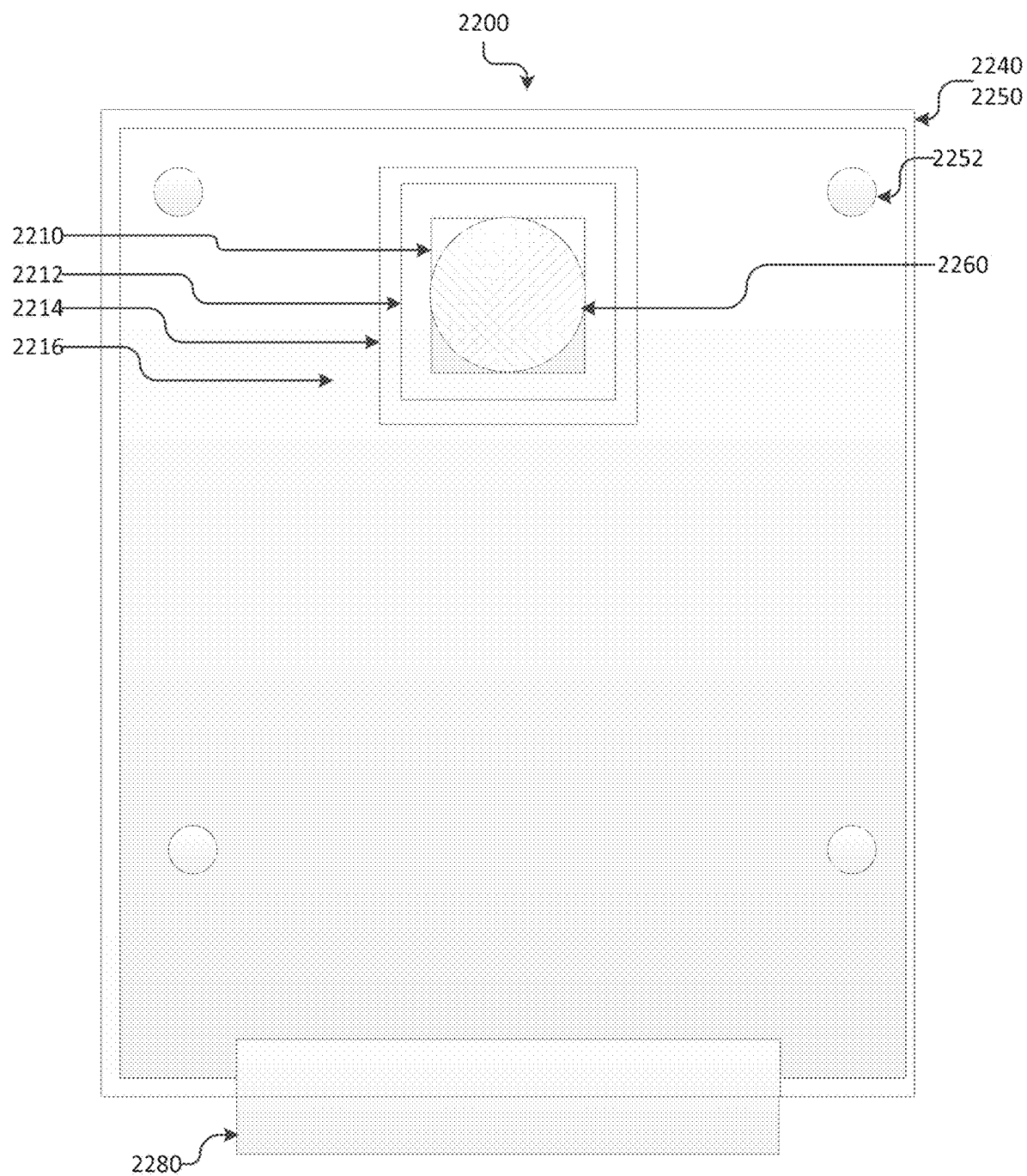
FIG. 22 illustrates a top view of an example DNA sequencing device consistent with embodiments disclosed herein.

FIG. 22 illustrates an example DNA sequencing device 2200 in accordance with the present disclosure. The DNA sequencing device 2200 is substantially similar to the biological sample analysis device described above with respect to FIGS. 1-18. The DNA sequencing device 2200 includes a first cartridge half 2240 and a second cartridge half 2250. The first cartridge half 2240 and the second cartridge half 2250 may be attached in a manner similar to the biological sample analysis device 100 discussed above with respect to FIG. 1.

As shown in FIG. 22, the first cartridge half 2240 includes an open-air well 2260. In various embodiments, a plurality of open-air wells 2260 may be included in the first cartridge half 2240. In some embodiments, ninety-six (96) open-air wells 2260 may be included in the first cartridge half 2240, similar to standard DNA sequencing plates. The open-air well 2260 serves the same function as the sample chamber 160 discussed above in FIG. 1. The bottom of the open-air wells 2260 are aligned with the sensor chips 2210 such that the open-air wells 2260 are in fluidic communication with the sensor chips 2210 to direct a suspension containing DNA molecules to the sensor chip 2210. A suspension is a liquid solution containing a DNA sample, for example cellular material from a cheek swab. In some embodiments, open-air well 2260 may include an O-ring groove on its outer rim, allowing a liquid-tight seal to form with the sensor chip 2210, similar to the seal discussed above with respect to FIG. 1. In various embodiments, a gasket may be placed in between the open-air wells 2260 and the sensor chips 2210 to seal the open-air wells 2260 and prevent the suspension from seeping into the rest of the DNA sequencing device 2200. In some embodiments, a cover (not pictured) may be included on the first cartridge half 2240. The cover may be configured to enclose the one or more open-air wells 2260 such that no liquid escapes if the DNA sequencing device 2200 is moved.

Still referring to FIG. 22, the second cartridge half 2250 may include a sensor chip 2210, a chip carrier 2212, a carrier socket 2214, a circuit board 2216, and an external connector 2280. For example, circuit board 2216 may be mounted or form fit inside of the second cartridge half 2250 and may be electronically coupled to external connector 2280. Circuit board 2216 may also support and electronically couple to carrier socket 2214, which in turn may support and electronically couple to chip carrier 2212. Chip carrier 2212 may be configured to physically support and electronically couple to sensor chip 2210. In various embodiments, the electrical connector 2280 may be coupled to an amp meter, voltmeter, multi-meter, or another external measurement device for monitoring the change in current or voltage of the transistors. In some embodiments, the electrical connector 2280 may be coupled to a computing device designed to measure current and voltage changes in the transistors due to changes in pH. In some embodiments, the electrical connector 2280 may both provide electricity to the circuit board 2216 and output signals to a device for monitoring, such as a computing device.

Where a plurality of open-air wells are included in the first cartridge half 2140, additional sensor chips 2210 may be required. In such embodiments, the circuit board 2216 may include a plurality of sensor chips 2210, chip carriers 2212, and carrier sockets 2214. Each sensor chip 2210 corresponds to one of the open-air wells 2260 included in the first cartridge half 2240. As discussed above, each sensor chip 2210 is configured to form a liquid-tight seal with one of the open-air wells 2260.

In various embodiments, sensor chip 2210 may be a Graphene chip with one or more Graphene transistors, similar to the Graphene chip discussed above in regards to FIGS. 17-18. Unlike traditional silicon transistors, Graphene does not oxidize in air, is extremely chemically inert, and thermally stable without the need for disposing protective layers on the Graphene. Accordingly, less material is necessary to construct the Graphene chip, and the Graphene chip may be placed directly in contact with the sensing environment.

The Graphene chip used as the sensor chip 2210 may comprise a plurality of electronic scattering sites, with each scattering site located on a particular Graphene transistor. Sequencing probes may be associated with each scattering site and Graphene transistor. In various embodiments, each scattering site may include covalently bonded sequencing probes that are complimentary to specific nucleotide sequences in the suspension. The sequencing probe may be bonded to the Graphene using a linker such as EDC and NHS, discussed above with regards to FIG. 18. In some embodiments, the sequencing probes may not be covalently bonded to the scattering sites, but instead immobilized through bonding to a structure directly adjacent to the Graphene transistor. For example, an immobilization layer of hydrogel or other adherent may be disposed on the Graphene chip 2210, and the sequencing probes may be disposed on the immobilization layer. Sensor chips capable of sequencing all possible base pair possibilities in accordance with the present disclosure can be constructed using high end electronics fabrication techniques, such as the photolithography fabrication process discussed above with regards to FIG. 18.

In various embodiments, the sensitivity of the sensor chip 2210 may be tailored by employing a similar protein binding method discussed above with respect to FIG. 18. Through tailoring the sensitivity of the sensor chip 2210, the DNA sequencing device 2200 may be optimized for a particular pH range. In various embodiments, the voltage shift measurements described above may be used. In some embodiments, the suspension itself may be optimized for a more sensitive reading by selecting solutions that interact more closely with the sensor chip 2210.

In various embodiments, additional calculations may be used to determine the effect of pH change and, accordingly, conduct DNA sequencing. Due to the unique properties of the Graphene used in creating the sensor chip 2210, the effects of pH changes on Graphene are more complex than those seen with typical semiconductor sensors, such as the ISFET. This complexity arises from the fact that the sensor chip 2210 is in direct contact with the sensing environment. In addition, the unique electronic structure of Graphene also contributes to the complexity. Graphene acts as a bipolar transistor, showing electronic characteristics of both n-type and p-type semiconductors. In some embodiments, changes in the transconductance of the Graphene may be used to determine the pH change. Transconductance is the ratio of the current variation at an output to the voltage variation at an input. The transconductance of a transistor is different at different pH levels. In some embodiments, changes in the resistance of the Graphene may be used. In other embodiments, a combination of one or more of the changes in current, transconductance, or resistance due to changes in pH may be used to identify the DNA sequence present in a suspension.

Figure 23:
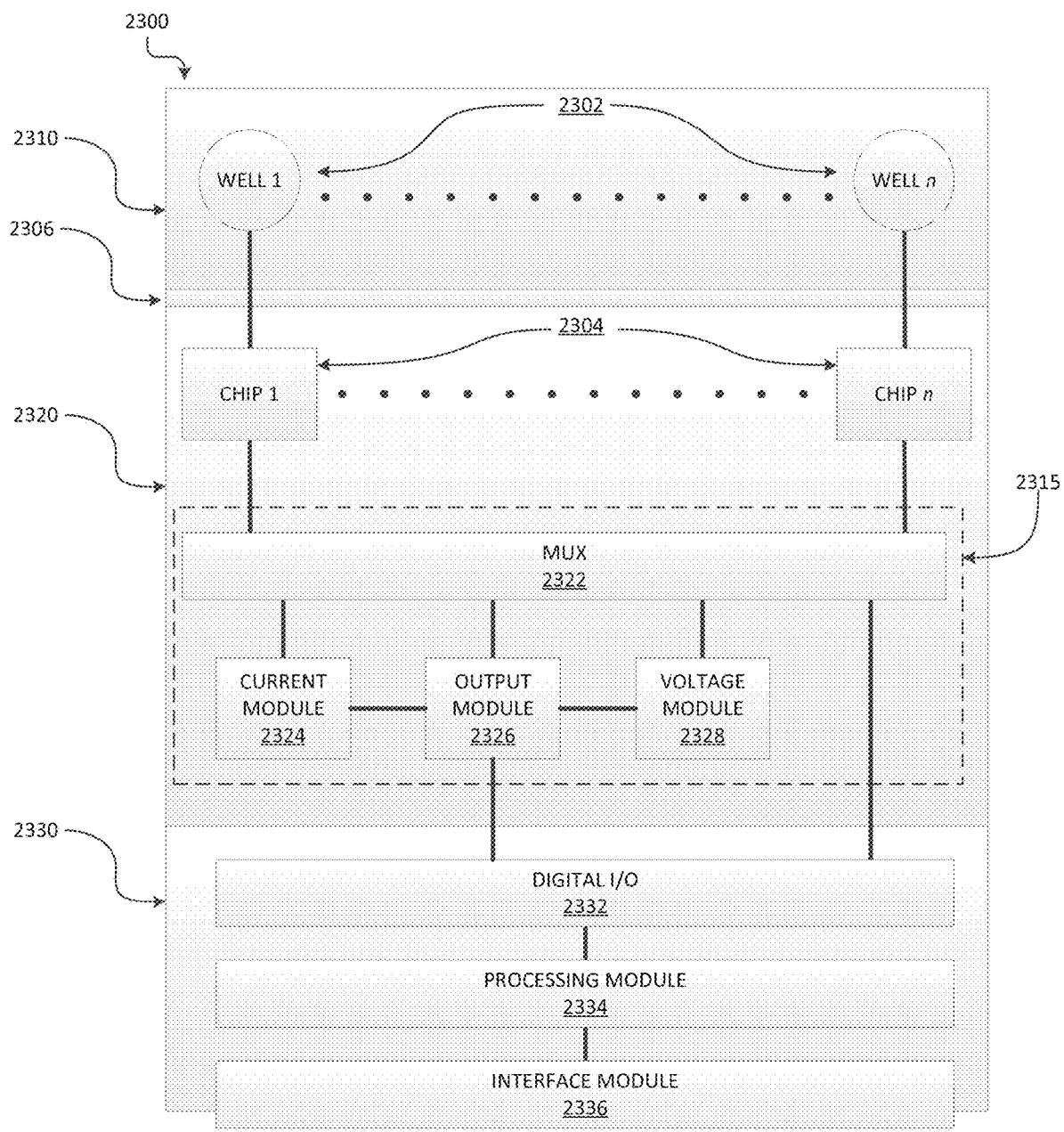
FIG. 23 is a block diagram illustrating another example DNA sequencing device consistent with embodiments disclosed herein.

In various embodiments, it may be beneficial to include some additional processing functionality within the DNA sequencing device itself. FIG. 23 is a block diagram illustrating another example DNA sequencing device 2300 in accordance with the present disclosure. As shown in FIG. 23, the DNA sequencing device 2300 includes a plate section 2310, which includes one or more open-air wells 2302, similar to the open-air wells 2260 described above with regards to FIG. 22. In some embodiments, the plate section 2310 may include ninety-six (96) open-air wells, similar to standard DNA sequencing plates. In some embodiments, the plate section 2310 may include a cover to seal the open-air wells 2302. In various embodiments, the cover may be attached to the plate section 2310 permanently. In other embodiments, the cover may be removable from the plate section 2310. In some embodiments, the cover may comprise individual strips configured to seal one or more open-air wells 2302 within a single column or row. In some embodiments, the plate section 2310 may be removable from the DNA sequencing device 2300. By removing the plate section 2310, cleaning the open-air wells 2302 and the sensor chips 2304 may be accomplished easier. In addition, if the plate section 2310 was to be damaged, but the rest of the device was unaffected, a user may be able to swap out an undamaged plate section for the damages section.

Each of the one or more open-air wells 2302 is configured to sit on top of a sensor chip 2304 embodied in a sensing section 2320. When situated on top of one of the sensor chips 2304, a suspension containing a DNA strand may be directed into the open-air well 2302 and the suspension can contact the sensor chip 2304, similar to the configuration discussed above with regards to FIG. 22. A liquid-tight seal 2306 is formed between each open-air well 2302 and sensor chip 2304. This liquid-tight seal 2306 may be formed in a similar manner as the seal discussed above with regards to FIG. 22. As configured, each sensor chip 2304 can sense changes in current and resistance in the suspension directed into the open-air well 2302 when a nucleotide sequence in the DNA is present that is complimentary to the sequencing probe associated with the transistor.

The output from each sensor chip 2304 may be fed into a data acquisition module (DAQ) 2315. The DAQ 2215 may serve the same purpose as the external amp meter, voltmeter, or multi-meter discussed above with regards to the electrical connector in FIG. 22. The DAQ 2215 may include a multiplexer module (MUX) 2322. The MUX enables analysis of multiple samples to occur using a single DNA sequencing device 2300 by allowing a user to select which of the samples to analyze by selecting the specific open-air well 2302 and sensor chip 2304 combination. In some embodiments, the DAQ may include a current module 2324 and a voltage module 2328. The current module 2324 may be configured to identify the change in current over time based on the output signal of one of the sensor chips 2304. The voltage module may be configured to identify the change in voltage over time based on the output signal of one of the sensor chips 2304. In various embodiments, the current module 2324 and the voltage module 2328 may convert the analog signals received from the sensor chips 2304 into digital signals for processing. In some embodiments, the DAQ may include an output module 2326 to combine the output from the current module 2324 and the voltage module 2328 and output the data to a digital I/O module 2332 embodied in the processing section 2330. In some embodiments, the output module 2326 may convert the output from the current module 2324 and the voltage module 2328 into digital signals. In some embodiments, the MUX 2322 of the DAQ 2315 may also communicate with the digital I/O module 2332.

In addition to the digital I/O module 2332, the processing section may include a processing module 2334 and an interface module 2336. The digital I/O module 2332 may provide a connection between the DAQ 2315 and the processing module 2334. The processing module may be configured to process the received digital signals from the digital I/O module 2332. In some embodiments, the processing module 2334 may be configured to determine the transconductance of the sensor chip 2304 for the sample being analyzed. In other embodiments, the processing module 2334 may be configured to determine the resistance of the sensor chip 2304. In some embodiments, the processing module 2334 may be configured to identify a DNA sequence present in a suspension based on the changes in the electrical properties of a transistor with an associated sequencing protein. The change in electrical properties indicates the presence of DNA binding, indicating that the complimentary nucleotide sequence to the particular sequencing protein is in the suspension. In some embodiments, the processing module 2334 may be configured to plot the change in pH over time against one or more of the change in current, voltage, transconductance, and resistance. In some embodiments, the processing module 2334 may include a memory configured to store the instructions relevant to each of the above described processing functions for the processing module 2334.

The interface module 2336 may be configured to output the data from the processing module 2336 to the user. In some embodiments, the interface module 2336 may include a connector configured to connect with a computing device. For example, in some embodiments, the interface module may include a USB connector, a VGA connector, a parallel port connector, or some other connector configured to transmit data to a computing device. In other embodiments, the interface module 2336 may include components for wireless transmission of data, such as Wi-Fi or Bluetooth. The user may control and interact with the DNA sequencing device 2300 through the interface module 2336.

In various embodiments, the processing section 2330 may be included on the same circuit board as the sensing section 2320. In other embodiments, the sensing section 2320 may be embodied on a first circuit board, and the processing section 2330 may be embodied on a section circuit board. In such embodiments, the sensing section 2320 circuit board may be connected to the processing section 2330 circuit board through pin headers. In other embodiments, the two boards may be connected directly by disposing pin headers on both boards configured to mate with each other. In other embodiments, a connecting cable may be used to connect one pin header on the sensing section 2320 with a pin header on the processing section 2330. One of ordinary skill would appreciate that any acceptable method of connecting the two circuit boards together may be utilized, depending on the design of the DNA sequencing device 2300.

Figure 24:
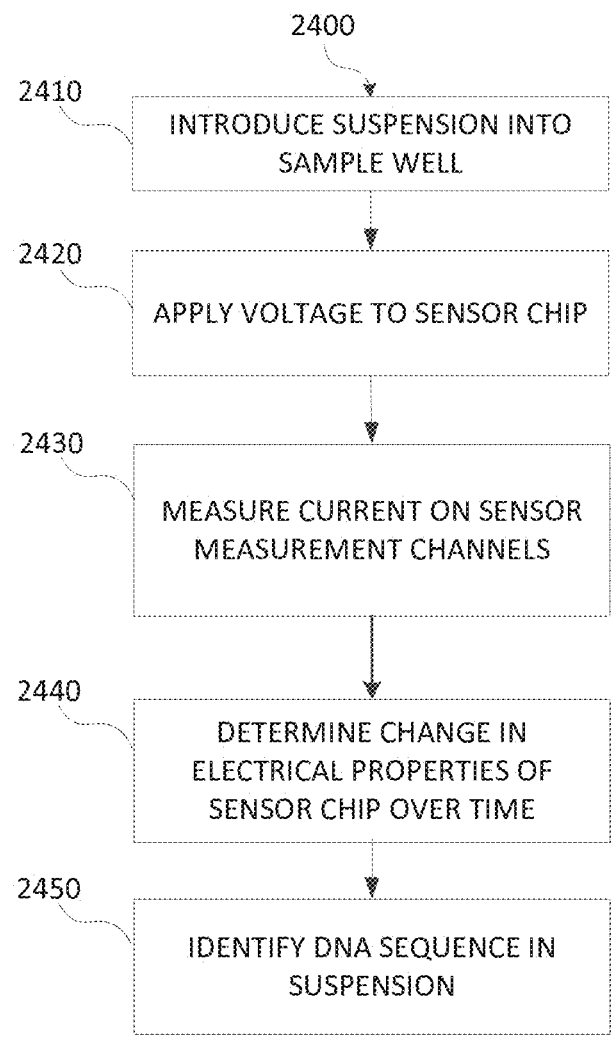
FIG. 24 is a process diagram illustrating a method for DNA sequencing consistent with embodiments disclosed herein.
Figure 25A:
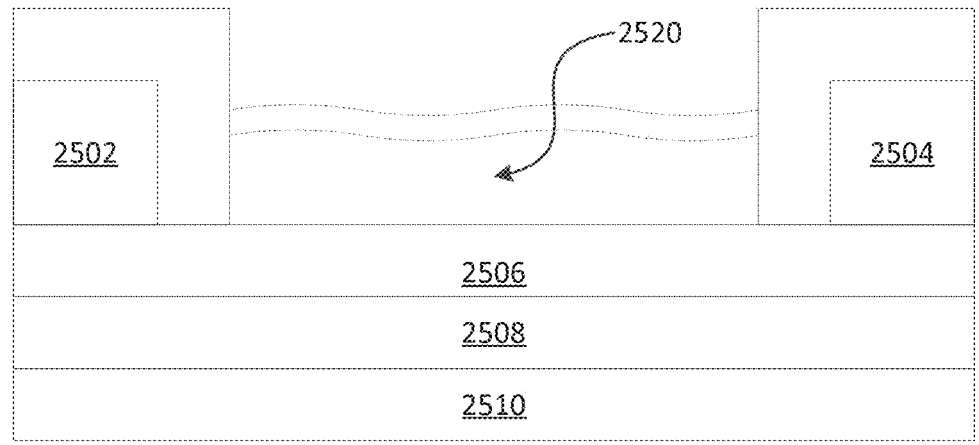
FIG. 25A is a cross-section diagram illustrating an example transistor sensor with a buffer layer, but without a sensitization layer.
Figure 25B:
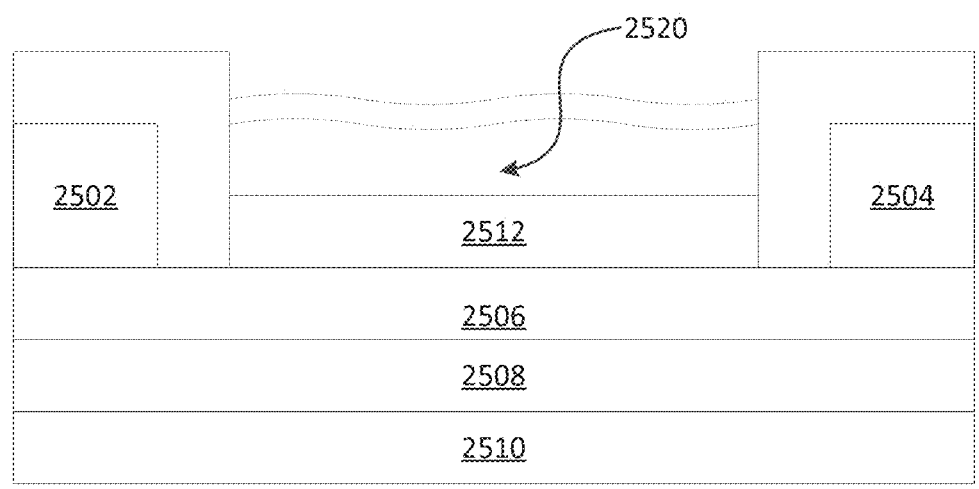
FIG. 25B is a cross-section diagram illustrating an example transistor sensor with a buffer layer and a sensitization layer.

FIG. 24 is a process diagram illustrating an example method of identifying DNA sequences (e.g. utilizing a DNA sequencing device). A method of identifying DNA sequences 2400 may include introducing a suspension into a sample well including a sensor chip at step 2410. The suspension may be DNA material, such as cellular material from a cotton swab, suspended in a liquid buffer as is known in the art. The sample well and sensor chip may be similar to the embodiments disclosed in FIGS. 22 and 23. Method 2400 may further include applying a voltage to the sensor chip at step 2420. In some embodiments, the voltage across the sensor chip may be held constant while the voltage across the liquid gate is varied during the measurement period. In other embodiments, the liquid gate voltage may be held constant, while the voltage across the sensor chip is varied.

In some embodiments, the voltage applied at step 2420 may be used to denature the DNA molecules within the suspension, if necessary. Method 2400 may further include measuring the current of the sensor chip on sensor measurement channels at step 2430. For example, each sensor measurement channel may be monitored through connector leads electronically coupled to corresponding transistors. In some embodiments, the method 2400 may be preceded by a calibration step, whereby solutions of known pH are introduced into the sample wells in order to determine the baseline reading for the sensor chip. Method 2400 may further include determining any change in the electrical properties of the sensor chip over time at step 2440. Changes in the transconductance and the resistance of the sensor chip indicates a release of a hydrogen ion around the sensor chip, changing the pH level. Method 2400 may further include identifying a DNA sequence of the DNA molecule in the suspension based on the change in electrical properties of the sensor chip at step 2450. The DNA sequence of a DNA molecule in a suspension is determinable by identifying the sequencing probe associated with the sensor chips in which the electrical properties changed over time, indicating a DNA binding process by the change in the pH.

The steps of measuring current on sensor measurement channels 2430, determine change in electrical properties over time 2440, and identifying the DNA sequence in the suspension 2460 may be performed by an electronic biological sample testing module. For example, a biological sample testing module may be a computer module as disclosed in FIG. 25 that includes a processor programmed with one or more computer programs configured to perform the steps disclosed herein. Other steps of method 2400 may be similarly performed by a computer module.

FIG. 25A is a cross-section diagram illustrating a transistor sensor with a buffer layer, but without a sensitization layer. As illustrated, source 2502 and drain 2504 are layered on channel 2506. Each of source 2502 and drain 2504 are fabricated from a semiconductor material (i.e., n-type or p-type semiconductors) and covered by an insulating material, as would be known in the art. Channel 2506, also fabricated from a semiconductor material, is layered on gate dielectric 2508, and gate dielectric 2508 is layered on back gate 2510. In this type of configuration, the channel 2506 generally will react with air or water, and thus a barrier layer (not shown) is typically deposited on top of the channel. For example, the barrier may be a metal oxide to prevent reactions in the channel. This barrier layer decreases the sensitivity of the transistor. In an array of this type of transistor illustrated in FIG. 25A, the barrier layer is generally deposited uniformly across the entire array of transistors. Environmental gate 2520 may be a water solution or alcohol solution, for example, that incorporates a biological or chemical sample.

FIG. 25B is a cross-section diagram illustrating a transistor sensor with a buffer layer and a sensitization layer. The structure of this transistor is the same as the structure illustrated in FIG. 25A, except a sensitization layer 2512 is layered on top of channel 2506 to increase sensitivity to targeted environmental gate solutions.

Figure 26A:
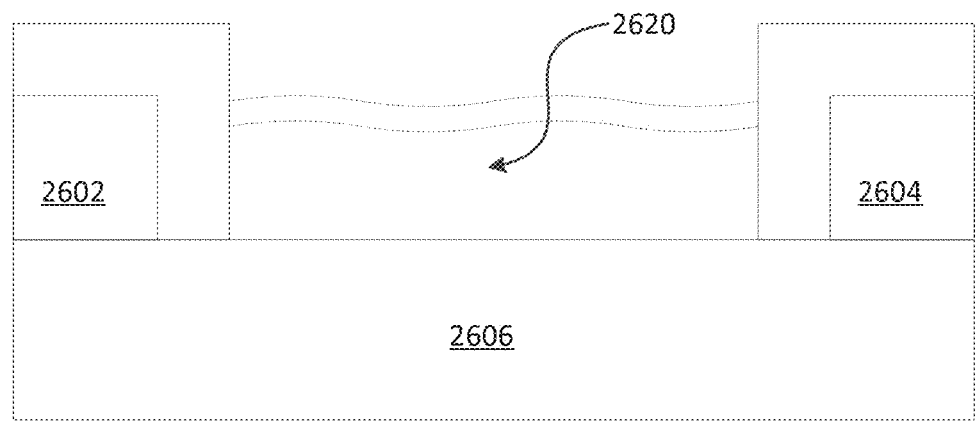
FIG. 26A is a cross-section diagram illustrating an example environmentally gated transistor sensor without a buffer layer or a sensitization layer, consistent with embodiments disclosed herein.

FIG. 26A is a cross-section diagram illustrating an environmentally gated transistor sensor without a buffer layer or a sensitization layer. The structure illustrates incorporates a channel substrate 2606 that fabricated from a semiconductor material that is chemically inert to air or water, with a source 2602 and drain 2604 layered thereon. For example, source 2602 and drain 2604 may each be fabricated from a semiconductor material (i.e., a n-type or p-type semiconductor), and the channel substrate 2606 may be fabricated from a Carbon-based semiconductor material such as Graphene or Carbon nanotubes. Environmental gate 2620 may be a liquid, such as a water-based solution, an alcohol-based solution, or a liquid metal, as disclosed herein. Source 2602 and drain 2604 are covered by an insulator to electrically insulate them from environmental gate 2620. Under this construction, no barrier layer is required, as the Carbon-based semiconductor is chemically inert to air and water. Source 2602 and drain 2604 are separated by a gap.

Based on electrical principles of transistors, when a sufficient threshold voltage is applied across the environmental gate 2620 and the source 2602, or the environmental gate 2620 and the drain 2604, current flow increases through channel 2606 and can be measured across leads (not shown) coupled to source 2602 and drain 2604. A gate electrode may be placed in, or in contact with environmental gate 2620 to apply a gate voltage. In some embodiments, the gate electrode may also be used as a sense electrode, e.g., to monitor changes in electrical properties of the environmental gate as gate voltage is applied.

Figure 26B:
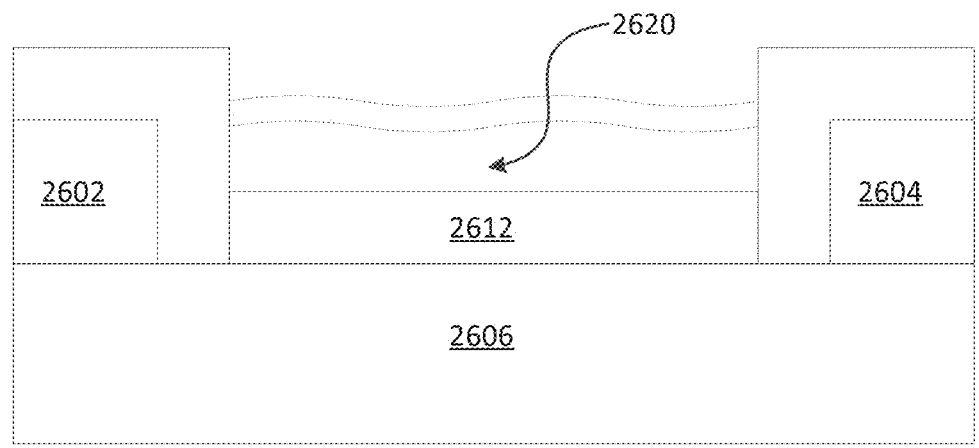
FIG. 26B is a cross-section diagram illustrating an example environmentally gated transistor sensor without a buffer layer, but with a sensitization layer, consistent with embodiments disclosed herein.

FIG. 26B is a cross-section diagram illustrating an environmentally gated transistor sensor with a buffer layer, like the transistor illustrated in FIG. 26A, but also including a sensitization layer 2612. For example, the sensitization layer 2612 may be a polymer or a protein. Different sensitization layers may be used to target different types of environmental gate substances (i.e., to increase sensitivity and specificity of a particular environmentally-gated transistor to a particular sample(s) within the environmental gate). By changing the composition or dimensions of the sensitization layer, the environmental gate's interaction with the channel substrate will change, and thus change the electrical properties of the environmentally-gated transistor. By varying the dimensions and compositions of the sensitization layers for different environmentally-gated transistor's in the array, the array can be sensitive to, and distinguish between many different substances within the environmental gate (i.e., biological molecules, antibodies, chemicals, etc.).

Figure 27:
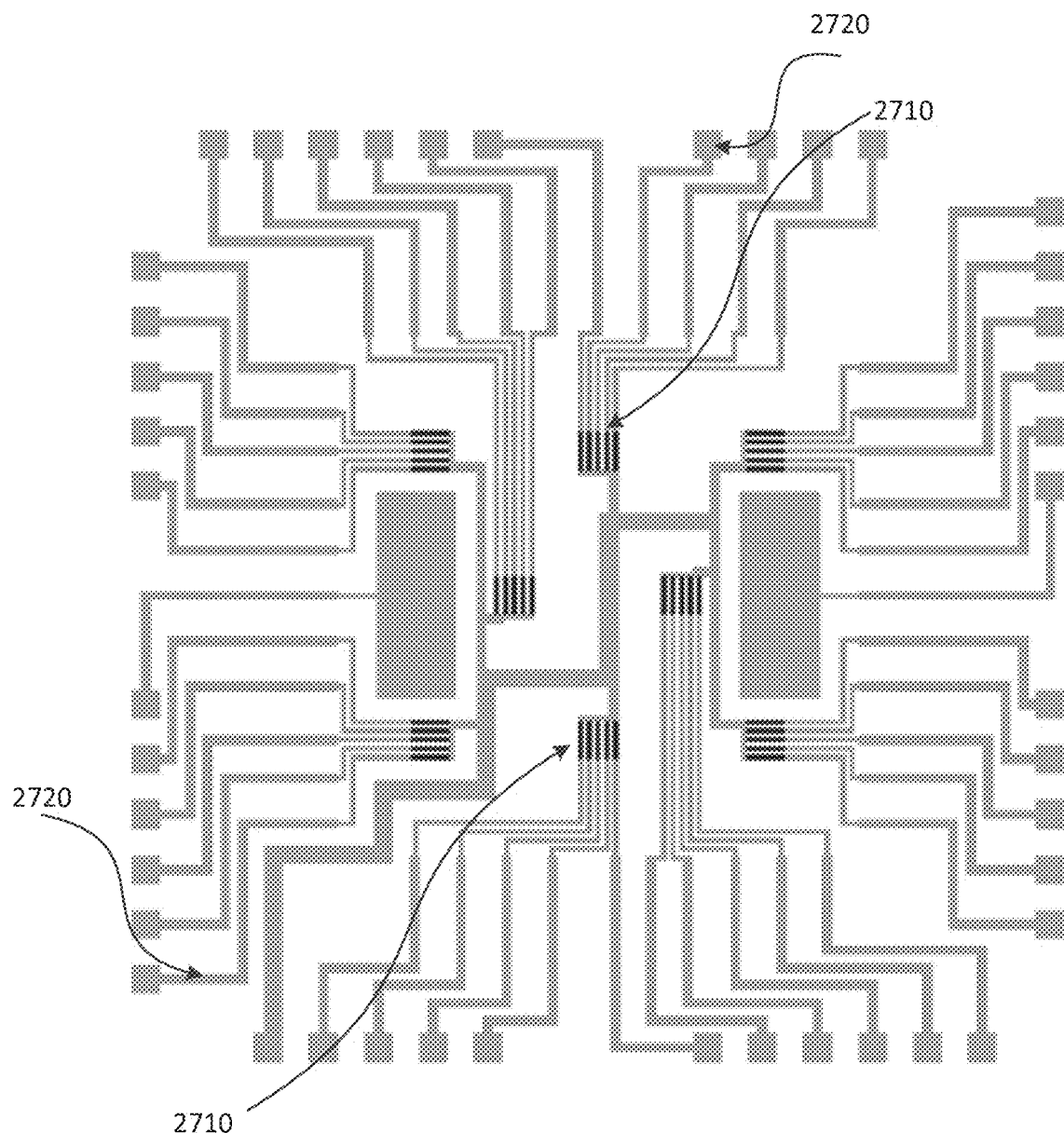
FIG. 27 is a top-down diagram illustrating an example arrayed sensor consistent with embodiments disclosed herein.

FIG. 27 is a top-down diagram illustrating an example arrayed sensor. As illustrated, electrical connections 2720 connect to the source and drain leads for environmentally gated transistors 2710. As illustrated, many (from just two, to thousands or more) environmentally gated transistors may be fabricated on a single array on the same Carbon-based substrate. One of ordinary skill in the art would appreciate that the example illustrated in FIG. 27 is only one type of possible layout for the environmentally-gated transistor array, and many other layouts and configurations are possible.

As discussed above, the system may also include an electrical measurement device (not shown) electrically coupled to the source lead or drain lead of each environmentally-gated transistors. For example, the electrical measurement device may be a voltmeter, an ampmeter, or other electrical measurement device configured to measure voltage, on-site resistance, or transconductance, or other electrical properties of the transistor. One of skill in the art would understand how to configure such an electrical measurement device across an array of transistors. In some examples, the electrical measurement device is also coupled to a computing module that is configured to receive an output signal from the electrical measurement device indicating an electrical measurement value, and the identify a composition of the environmental gate based on the output signal. The computing module may include a processor and memory with a software program embedded thereon, the software being configured to perform the measurement and identification steps described above. In some examples, the computing module may also include a display and a user input device (e.g., a keyboard, mouse, etc.) to enable user interaction.

Figure 28:
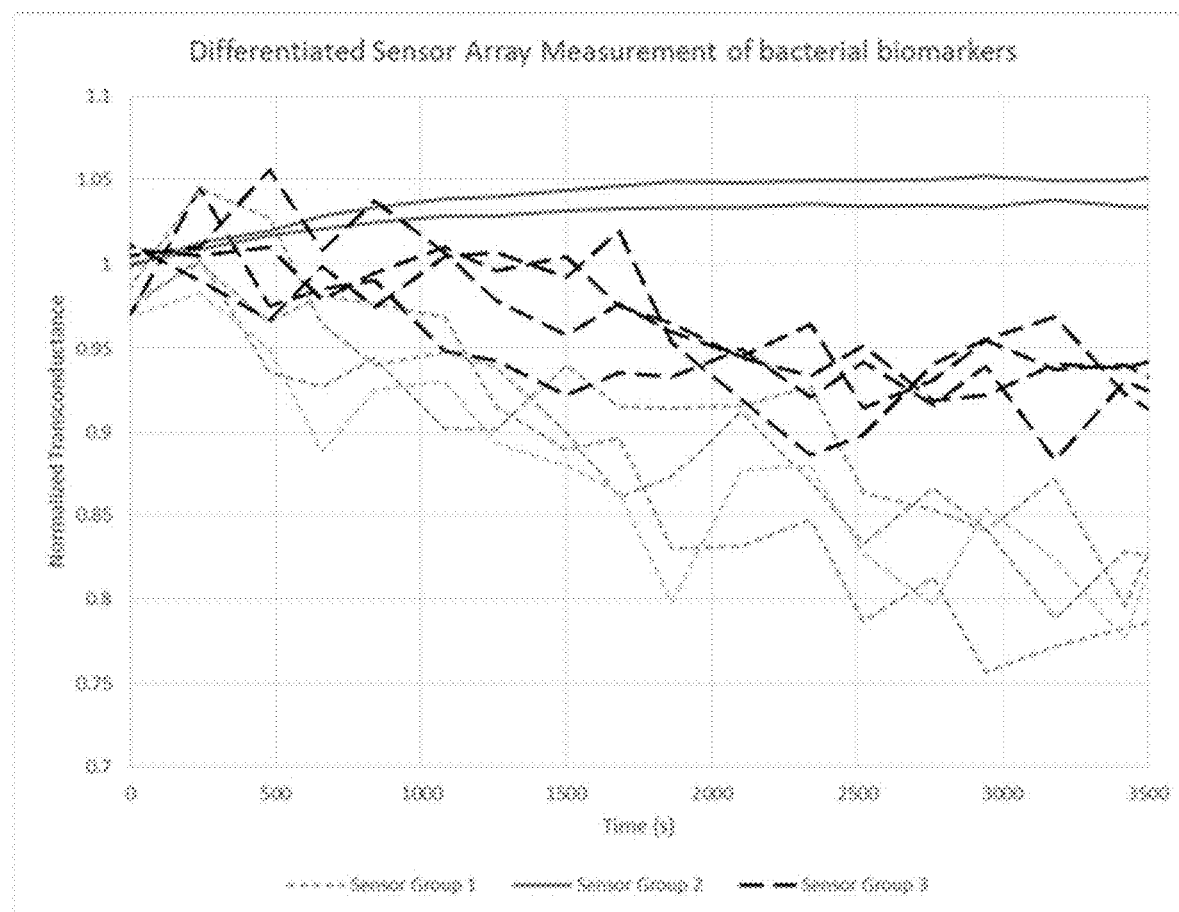
FIG. 28 is a chart illustrating sensor array measurements of a biological sample using different sensor groupings with different sensitization layers.

FIG. 28 is a chart illustrating sensor array measurements of a biological sample using different sensor groupings with different sensitization layers. For example, a similar chart may be generated using the computing module described above. Referring to FIG. 28, the y-axis of the chart is normalized transconductance and the x-axis is time. An environmental gate solution containing multiple bacterial biomarkers is exposed to the array of environmentally-gated transistors, wherein environmentally-gated transistors in sensor group 1 includes a first sensitization layer 2612 sensitive to a first type of biomarker, environmentally-gated transistors in sensor group 2 includes a second sensitization layer 2612 sensitive to a second type of biomarker, and environmentally-gated transistors in sensor group 3 includes a third sensitization layer 2612 sensitive to a third type of biomarker. Example transconductance measurements across the sensor array for all three sensor groups over time are illustrated on the chart, demonstrating the ability of the array to quickly detect and identify different biomarkers.

Figure 29:
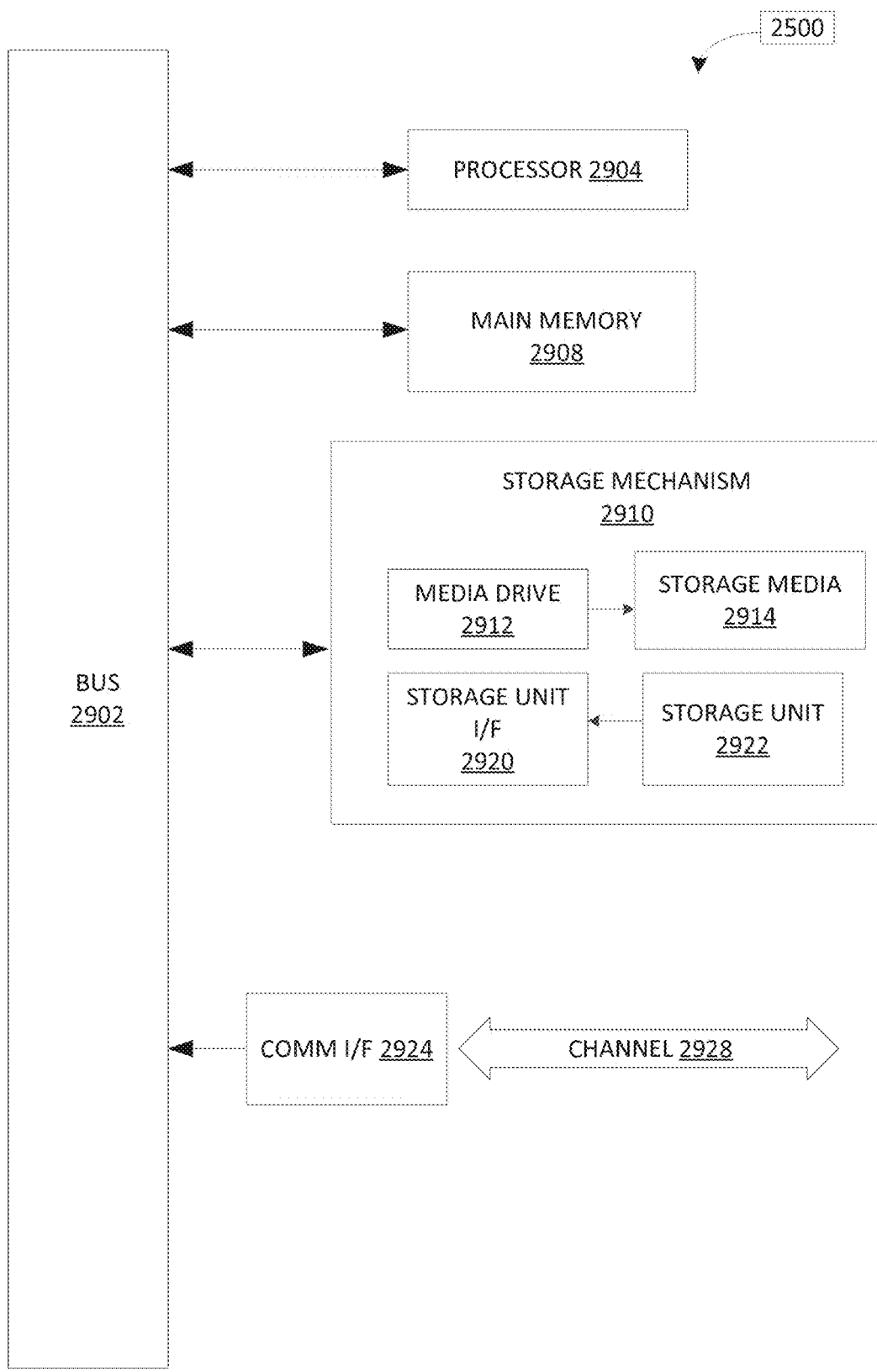
FIG. 29 illustrates an example-computing module that may be used to implement various features of the systems and methods disclosed herein.

FIG. 29 illustrates an example computing module that may be used to implement various features of the systems and methods disclosed herein. In one embodiment, the computing module includes a processor and a set of computer programs residing on the processor. The set of computer programs may be stored on a non-transitory computer readable medium having computer executable program code embodied thereon. The computer executable code may be configured to perform one or more steps of the method for electronically testing a biological sample 1900 disclosed in FIG. 19, one or more steps of the method for electronic biological sample analysis 2000 disclosed in FIG. 20, and/or one or more steps of the method for DNA sequencing 2400 disclosed in FIG. 24. The computer executable code may further be configured to measure, detect, and identify environmental gate compositions based on measured electrical properties across a chemically differentiated sensor array, consistent with the environmentally-gated transistors and array illustrated in FIGS. 26A, 26B, and 27.

As used herein, the term module might describe a given unit of functionality that can be performed in accordance with one or more embodiments of the present application. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one embodiment, these software elements can be implemented to operate with a computing or processing module capable of carrying out the functionality described with respect thereto. One such example computing module is shown in FIG. 29. Various embodiments are described in terms of this example-computing module 2900. After reading this description, it will become apparent to a person skilled in the relevant art how to implement the application using other computing modules or architectures.

Referring now to FIG. 29, computing module 2900 may represent, for example, computing or processing capabilities found within desktop, laptop, notebook, and tablet computers; hand-held computing devices (tablets, PDA's, smart phones, cell phones, palmtops, smart-watches, smart-glasses etc.); mainframes, supercomputers, workstations or servers; or any other type of special-purpose or general-purpose computing devices as may be desirable or appropriate for a given application or environment. Computing module 2900 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 2900 might include, for example, one or more processors, controllers, control modules, or other processing devices, such as a processor 2904. Processor 2904 might be implemented using a general-purpose or special-purpose processing engine such as, for example, a microprocessor, controller, or other control logic. In the illustrated example, processor 2904 is connected to a bus 2902, although any communication medium can be used to facilitate interaction with other components of computing module 2900 or to communicate externally.

Computing module 2900 might also include one or more memory modules, simply referred to herein as main memory 2908. For example, preferably random access memory (RAM) or other dynamic memory, might be used for storing information and instructions to be executed by processor 2904. Main memory 2908 might also be used for storing temporary variables or other intermediate information during execution of instructions to be executed by processor 2904. Computing module 2900 might likewise include a read only memory ("ROM") or other static storage device coupled to bus 2902 for storing static information and instructions for processor 2904.

The computing module 2900 might also include one or more various forms of information storage mechanism 2910, which might include, for example, a media drive 2912 and a storage unit interface 2920. The media drive 2912 might include a drive or other mechanism to support fixed or removable storage media 2914. For example, a hard disk drive, a solid state drive, a magnetic tape drive, an optical disk drive, a CD or DVD drive (R or RW), or other removable or fixed media drive might be provided. Accordingly, storage media 2914 might include, for example, a hard disk, a solid state drive, magnetic tape, cartridge, optical disk, a CD or DVD, or other fixed or removable medium that is read by, written to or accessed by media drive 2912. As these examples illustrate, the storage media 2914 can include a computer usable storage medium having stored therein computer software or data.

In alternative embodiments, information storage mechanism 2910 might include other similar instrumentalities for allowing computer programs or other instructions or data to be loaded into computing module 2900. Such instrumentalities might include, for example, a fixed or removable storage unit 2922 and a storage interface 2920. Examples of such storage units 2922 and storage interfaces 2920 can include a program cartridge and cartridge interface, a removable memory (for example, a flash memory or other removable memory module) and memory slot, a PCMCIA slot and card, and other fixed or removable storage units 2922 and storage interfaces 2920 that allow software and data to be transferred from the storage unit 2922 to computing module 2900.

Computing module 2900 might also include a communications interface 2924. Communications interface 2924 might be used to allow software and data to be transferred between computing module 2900 and external devices. Examples of communications interface 2924 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 2924 might typically be carried on signals, which can be electronic, electromagnetic (which includes optical) or other signals capable of being exchanged by a given communications interface 2924. These signals might be provided to communications interface 2924 via a channel 2928. This channel 2928 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, memory 2908, storage unit 2920, media 2914, and channel 2928. These and other various forms of computer program media or computer usable media may be involved in carrying one or more sequences of one or more instructions to a processing device for execution. Such instructions embodied on the medium are generally referred to as "computer program code" or a "computer program product" (which may be grouped in the form of computer programs or other groupings). When executed, such instructions might enable the computing module 2900 to perform features or functions of the present application as discussed herein.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

While various embodiments of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present disclosure. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosure is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosure, whether or not such embodiments are described and whether or not such features are presented as being a part of a described embodiment. Thus, the breadth and scope of the present disclosure should not be limited by any of the above-described exemplary embodiments.

What is claimed is:

1. A sensor chip comprising:
a chemically-differentiated graphene field effect transistor array having a plurality of transistors, wherein:
each transistor in the array comprises a drain, a source, a substrate channel, and an environmental gate shared among the plurality of transistors in a well configured to receive a liquid sample;
the substrate channel comprises $sp^2$ hybridized carbon in the form of graphene and one or more electronic scattering sites, each scattering site comprising sp3 hybridized carbon chemically prepared to enable covalent bonding of a biomolecule to the substrate channel;
the drain electrically couples to a first location on the substrate channel and is formed using the same conductive layer that forms the drain of each of the plurality of transistors and bond pads or leads of the sensor chip;
the source electrically couples to a second location on the substrate channel separated by a gap from the first location on the substrate channel and is formed using the same conductive layer that forms the source of each of the plurality of transistors and the bond pads or leads of the sensor chip;
the environmental gate shared among the plurality of transistors is a liquid gate formed above the substrate channels of the plurality of transistors by receipt of the liquid sample in the well;
a first insulating layer covers and separates the drain from the environmental gate; and
a second insulating layer covers and separates the source from the environmental gate; and wherein:
a first group of one or more transistors of the plurality of transistors is functionalized with a first type of sensitization layer comprising a polymer that is not covalently bound to the channel and is selected to increase sensitivity of the transistor to a first type of biomolecule in the sample liquid forming the environmental gate a second group of one or more transistors of the plurality of transistors functionalized with a second type of sensitization layer selected from a protein selected to bind to an antibody in the liquid sample and an antibody selected to bind to a biomolecule in the liquid sample; and one or more gate electrodes offset horizontally from the channel of any of the plurality of transistors and electrically coupled to the environmental gate upon receipt of the liquid sample, the one or more gate electrodes operable to perform one or more operations selected from applying a voltage to the liquid forming the environmental gate and monitoring a resulting liquid voltage of the environmental gate as a reference voltage, wherein the chemically-differentiated graphene field effect transistor array is configured to enable respective measurement vectors to be determined for the differently functionalized transistors in each of said groups in response to binding events occurring between biomolecules in the shared environmental gate formed upon receipt of the liquid sample and the respective sensitization layers of said groups, the respective measurement vectors comprising a liquid gate voltage, an output current, and a slope indicative of the transconductance of said groups of transistors.

2. The sensor chip of claim 1, wherein the environmental gate comprises a water, alcohol, or metal.

3. The sensor chip of claim 1, wherein the environmental gate comprises a biological sample.

4. The sensor chip of claim 3, wherein the biological sample comprises blood.

5. The sensor chip of claim 3, wherein the biological sample comprises urine.

6. The sensor chip of claim 3, wherein the biological sample comprises bacterial growth media.

7. The sensor chip of claim 3, wherein the biological sample comprises food.

8. The sensor chip of claim 1, further comprising a third group of one or more transistors of the plurality of transistors functionalized with a third type of sensitization layer comprising a sequencing probe that is covalently bound directly or through a linker to the scattering sites on the substrate channel of the third group of transistors.

9. The sensor chip of claim 1, wherein each of said groups of transistors each comprise five or more transistors configured in a linear arrangement.

10. The sensor chip of claim 9, wherein at least one of the one or more gate electrodes is disposed between the first group of one or more transistors and the second group of one or more transistors.

11. A system comprising:
a printed circuit board;
a sensor chip electrically coupled to the circuit board, the sensor chip comprising:
a chemical-differentiated graphene field effect transistor array having a plurality of transistors, wherein:
each transistor in the array comprises a drain, a source, a substrate channel, and an environmental gate shared among the plurality of transistors in a well configured to receive a liquid sample; wherein:
the substrate channel comprises sp2 hybridized carbon in the form of graphene and one or more electronic scattering sites, each scattering site comprising sp3 hybridized carbon chemically prepared to enable covalent bonding of a biomolecule to the substrate channel;
the drain electrically couples to a first location on the substrate channel and is formed using the same conductive layer that forms the drain of each of the plurality of transistors and bond pad or leads of the sensor chip;
the source electrically couples to a second location on the substrate channel separated by a gap from the first location on the substrate channel and is formed using the same conductive layer that forms the source of each of the plurality of transistors and the bond pads or leads of the sensor chip;
the environmental gate shared among the plurality of transistors is a liquid gate formed above the substrate channels of the plurality of transistors by receipt of the liquid sample in the well;
a first insulating layer covers and separates the drain from the environmental gate; and
a second insulating layer covers and separates the source from the environmental gate; and wherein:
a first group of one or more transistors of the plurality of transistors is functionalized with a first type of sensitization layer comprising a polymer that is not covalently bound to the channel and is selected to increase sensitivity of the transistor to a first type of biomolecule in the sample liquid forming the environmental gate;
a second group of one or more transistors of the plurality of transistors functionalized with a second type of sensitization layer selected from a protein selected to bind to an antibody in the liquid sample and an antibody selected to bind to a biomolecule in the liquid sample; and
one or more gate electrodes offset horizontally from the channel of any of the plurality of transistors and electrically coupled to the environmental gate upon receipt of the liquid sample, the one or more gate electrodes operable to perform one or more operations selected from applying a voltage to the liquid forming the environmental gate and monitoring a resulting liquid voltage of the environmental gate as a reference voltage,
wherein the chemically-differentiated graphene field effect transistor array is configured to enable respective measurement vectors to be determined for the differently functionalized transistors in each of said groups in response to binding events occurring between biomolecules in the shared environmental gate formed upon receipt of the liquid sample and the respective sensitization layers of said groups, the respective measurement vectors comprising a liquid gate voltage, an output current, and a slope indicative of the transconductance of said groups of transistors.

12. The system of claim 11, further comprising a power supply and an electrical measurement device wherein the drains of each environmentally-gated transistor in the array are electrically connected together to electrically couple through a single lead to a power supply and the sources of each environmentally-gated transistors in the array are configured to individually connect through a multiplexer to an electrical measurement device.

13. The system of claim 11, wherein the sensor chip further comprises a third group of one or more transistors of the plurality of transistors functionalized with a third type of sensitization layer comprising a sequencing probe that is covalently bound directly or through a linker to the scattering sites on the substrate channel of the third group of transistors.

14. The system of claim 11, further comprising a processor configured to detect the presence of one or more biomarkers indicative of an infection involving a selected virus based on the measurement vectors associated with one or more of said groups of transistors.

15. The system of claim 14, wherein the one or more biomarkers indicative of the infection involving the selected virus are selected from an antibody to the selected virus, a protein associated with the selected virus, a nucleotide sequence associated with the selected virus; and combinations thereof.

16. The system of 15, wherein the selected virus is a type of SARS coronavirus.

17. The system of claim 11, wherein each of said groups of transistors each comprise five or more transistors configured in a linear arrangement.

18. The system of claim 14, wherein at least one of the one or more gate electrodes is disposed between the first group of one or more transistors and the second group of one or more transistors.

* * * * *